United States Patent
Kamenka et al.

(10) Patent No.: US 6,514,967 B1
(45) Date of Patent: Feb. 4, 2003

(54) COMPOUND FOR PREPARING MEDICINES FOR TREATING PATHOLOGIES INVOLVING EXTRACELLULAR GLUTAMATE, AND METHODS FOR OBTAINING SAME

(75) Inventors: Jean-Marc Kamenka, Montpellier (FR); Isoline Caubere, Montpellier (FR); Gerard Barbanel, Montpellier (FR)

(73) Assignee: Centre National de la Recherche Scientifique (FR)

( * ) Notice: Subject to any disclaimer, the term of this patent is extended or adjusted under 35 U.S.C. 154(b) by 0 days.

(21) Appl. No.: 09/424,208

(22) PCT Filed: May 22, 1998

(86) PCT No.: PCT/FR98/01029
§ 371 (c)(1),
(2), (4) Date: Dec. 16, 1999

(87) PCT Pub. No.: WO98/52936
PCT Pub. Date: Nov. 26, 1998

(30) Foreign Application Priority Data

May 22, 1997 (FR) .............................. 97 06265

(51) Int. Cl.$^7$ .................... C07D 333/54; C07D 333/50; A61K 31/381
(52) U.S. Cl. ................. 514/232.8; 514/233.5; 514/233.8; 514/254.11; 514/252.13; 514/321; 514/324; 514/432; 514/437; 514/443; 544/146; 544/376; 544/377; 544/378; 546/197; 546/202; 549/23; 549/43; 549/52; 549/54; 549/55
(58) Field of Search ................ 514/232.8, 233.5, 514/233.8, 254.11, 252.13, 321, 324, 432, 437, 443; 544/146, 376, 377, 378; 546/197, 202; 549/23, 43, 52, 54, 55

(56) References Cited

U.S. PATENT DOCUMENTS

| | | | | |
|---|---|---|---|---|
| 3,972,895 A | * | 8/1976 | Asato | 260/329 |
| 4,036,979 A | * | 7/1977 | Asato | 424/275 |
| 4,134,899 A | * | 1/1979 | Asato | 260/332.2 |
| 4,154,740 A | * | 5/1979 | Asato | 260/332.3 |
| 4,156,670 A | * | 5/1979 | Asato | 260/332.3 |
| 4,878,940 A | * | 11/1989 | De Bruyn et al. | 71/92 |
| 4,921,955 A | * | 5/1990 | Topfl | 544/60 |
| 4,994,103 A | * | 2/1991 | De Bruyn et al. | 71/92 |
| 5,684,020 A | * | 11/1997 | Peglion et al. | 514/320 |
| 5,753,662 A | * | 5/1998 | Peglion et al. | 514/254 |

FOREIGN PATENT DOCUMENTS

| | | | |
|---|---|---|---|
| EP | 0207563 | * | 1/1987 |
| EP | 0280268 | | 8/1988 |
| EP | 0289066 | * | 11/1988 |
| EP | 0314852 | * | 5/1989 |
| WO | 9005524 | | 5/1990 |
| WO | 9109032 | | 6/1991 |

OTHER PUBLICATIONS

Uematsu, N. et al., Assymetric Synthesis Hydrogenation of Imines, J. Am. Chem. Soc. 118(20), pp. 4916–4917. 1996.*
Uematsu, et al, "Asymmetric . . . Imines", J. Am. Chem. Soc. 1996, vol. 118 (20), pp. 4916–17, XP002080164.

* cited by examiner

*Primary Examiner*—Deepak Rao
(74) *Attorney, Agent, or Firm*—Bierman, Muserlian and Lucas

(57) ABSTRACT

The invention relates to compounds of the following general formula (I):

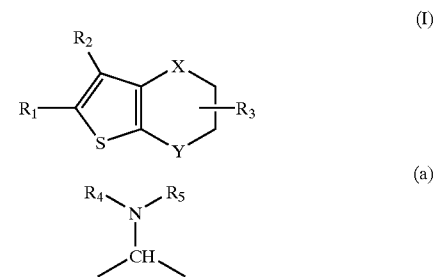

in which: $R_1$ and $R_2$ represent a hydrogen atom, or form a ring, especially a benzene ring, $R_3$ represents a hydrogen atom or an alkyl group, especially a methyl group, X and Y, independently of one another, represent a carbon atom, or a heteroatom such as a sulphur atom S, or a group with the formula (a) in which $R_4$ and $R_5$ represent a hydrogen atom or a methyl group, or $R_4$ and $R_5$ form a heterocycle, and their use for the preparation of a drug intended for the treatment of pathologies associated with abnormally high concentrations of extracellular glutamate.

20 Claims, 5 Drawing Sheets

COMPOUND FOR PREPARING MEDICINES FOR TREATING PATHOLOGIES INVOLVING EXTRACELLULAR GLUTAMATE, AND METHODS FOR OBTAINING SAME

This application is a 371 of PCT/FR98/01029 filed May 22, 1998.

The present invention relates to compounds with antiradical activity, as well as pharmaceutical compositions containing them, methods of obtaining them, and their use in the treatment of pathologies involving abnormally high concentrations of extracellular glutamate.

Neurotoxic concentrations of extracellular glutamate cause neuron death in various acute pathologies: traumatisms, ischaemias, exogenous intoxication. The same type of neuron death process also occurs during chronic neurodegenerative diseases: Alzheimer's disease, Parkinson's disease, amyotrophic lateral sclerosis.

Molecules that are able to antagonize the neurotoxic action of glutamate in the acute pathologies mentioned above were the subject of European patent application 0 396 734 dated Nov. 20, 1989. This relates to arylcyclohexylamines acting as noncompetitive antagonists of the N-methyl-D-aspartate (NMDA) receptor. This receptor, on which the glutamate acts, is responsible for massive entry of $Ca^{2+}$ ions into the neurons, in the presence of abnormally high concentrations of extracellular glutamate, which causes neuron death. These noncompetitive antagonists of NMDA attach themselves to the receptor of phencyclidine (PCP) and thus block entry of the $Ca^{2+}$ ions However, these molecules do not affect the extracellular concentration of glutamate, and are especially suitable for use in emergencies in the treatment of the aforementioned acute pathologies.

Recent Italian works tend to show that the release of free radicals derived from oxygen, which accompanies the release of glutamate, might amplify the deleterious action of the latter (Volterra A et al. Reactive oxygen species inhibit high-affinity glutamate uptake: molecular mechanism and neuropathological implications. Ann. N. Y. Acad. Sci. 738, 153–162 (1994). Volterra A et al. Glutamate uptake is inhibited by arachidonic acid and oxygen radicals via two distinct and additive mechanisms. Mol. Pharmacol. 46, 986–992 (1994). Volterra A et al. Glutamate uptake inhibition by oxygen free radicals in rat cortical astrocytes. J. Neurosci. 14, 2924–2932 (1994). Volterra A et al. Inhibition of high-affinity glutamate transport in neuronal and glial cells by arachidonic acid and oxygen-free radicals. Molecular mechanisms and neuropathological relevance. Ren Physiol Biochem 17, 165–167 (1994)).

In fact, the astrocytic transporter of glutamate, which is the principal mechanism of removal of extracellular glutamate by recapture, is inhibited by the action of the radicals. This leads to accumulation of glutamate, not only as a result of considerable release, but also, and perhaps predominantly, as a result of non-capture.

Radicals in the central nervous system (CNS) are now under investigation in numerous studies. Many molecules, often of natural origin, such as vitamin E, vitamin C, melatonin, derivatives of ginkgo biloba, and glutathion have been proposed as radical scavengers, as well as molecules obtained synthetically. The main problem to be solved is the tropism of these structures for the CNS. Since the sequence of formation of the radicals generally begins with the production of the superoxide anion, and a quite widely occurring enzyme (superoxide dismutase, SOD) has the task of destroying them during normal metabolism, this is under investigation in numerous studies. Direct use of this enzyme, suitably vectorized, is being tried. In particular, this is one of the routes envisaged for the treatment of amyotrophic lateral sclerosis of familial origin (Ikeda K. et al., 1995, 5(5), 383–390). It should be noted, however, that these enzyme vectorization techniques apply more especially to intracellular action, and so are likely to be accompanied by significant side effects.

The aim of the present invention is to provide compounds possessing the following main properties:
  easy and fast penetration of the CNS (lipophilic compounds that cross the blood-brain barrier),
  preferably little or no affinity for the receptor of PCP,
  no penetration into the cells (and therefore possessing extracellular action), which limits their field of action in any side effects,
  and ability to protect the glutamate transporter(s) of the astrocytes, by acting as scavengers of free radicals derived from oxygen in the extracellular space of the CNS. In this way, by protecting the still uninhibited transporters, recapture of astrocytic glutamate remains active, and thus able to limit the concentrations of glutamate and, in consequence, the neurotoxic effects.

It should be emphasized that the expression CNS used in the foregoing and hereinafter, comprises the brain, the cerebellum and the spinal cord.

Another aim of the invention is to provide pharmaceutical compositions that can be used in the treatment of pathologies affecting the CNS and involving abnormally high concentrations of extracellular glutamate.

Another aim of the invention is to provide methods of preparation of the said compounds and pharmaceutical compositions.

The invention relates to compounds that possess the aforementioned properties, with the following general formula (I):

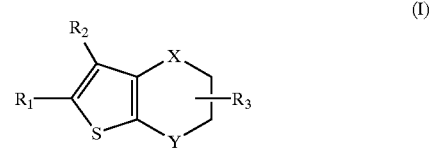

in which:
  $R_1$ and $R_2$, independently of one another, represent a hydrogen atom, an alkyl group with 1 to 5 carbon atoms, especially a methyl group, a hydroxyl group, a halogen atom, in particular an atom of chlorine, bromine, iodine or fluorine, or: $R_1$ and $R_2$ form, in conjunction with the carbon atoms carrying them, a substituted or unsubstituted, aromatic or non-aromatic ring, with 4 to 8 carbon atoms in the ring, especially a benzene ring,
  $R_3$ represents a hydrogen atom or an alkyl group with 1 to 5. carbon atoms, especially a methyl group,
  X and Y, independently of one another, represent $CH_2$, or a heteroatom such as a sulphur atom S, or a group with the formula

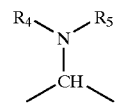

in which $R_4$ and $R_5$ represent, independently of one another, a hydrogen atom or an alkyl group with 1 to 5 carbon atom, especially a methyl group, or $R_4$ and $R_5$ form, in conjunction with the nitrogen atom carrying them, a substituted or unsubstituted, aromatic or non-aromatic heterocycle, with 4 to 8 carbon atoms in the ring, including if necessary an additional heteroatom in the ring, especially a ring with the formula

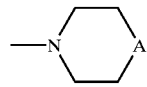

in which A represents:
a group

in which Z represents CH or N, $R_6$ represents a hydrogen atom or an alkyl group with 1 to 5 carbon atoms, especially a methyl group, or a hydroxyl group,
or a heteroatom such as O or S.

The invention relates more particularly to compounds of formula (I) mentioned above, in which at least either X or Y represents a group with the formula

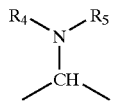

in which $R_4$ and $R_5$ are as defined above.

The invention relates more particularly to the compounds of formula (I) mentioned above, in which:
$R_1$ and $R_2$ represent a hydrogen atom, or $R_1$ and $R_2$ form, in conjunction with the carbon atoms that they carry, a benzene ring,
$R_3$ represents a hydrogen atom or an alkyl group with 1 to 5 carbon atoms, especially a methyl group,
either X or Y represents a group with the formula

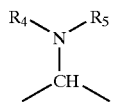

in which $R_4$ and $R_5$ represent a hydrogen atom, or $R_4$ and $R_5$ form, in conjunction with the nitrogen atom carrying them, a heterocycle with the formula:

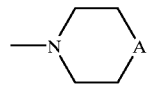

in which A represents:
a group

in which Z represents CH or N, $R_6$ represents a hydrogen atom, a methyl group, or a hydroxyl group,
or a heteroatom such as O or S.

The invention relates even more especially to compounds as defined above, with the following formula (II):

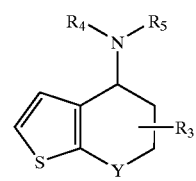

(II)

in which $R_3$, $R_4$, and $R_5$ have the meanings indicated above, and Y represents $CH_2$ or a sulphur atom S.

Particularly preferred compounds of formula (II) are those represented by the following formulae:

IC023

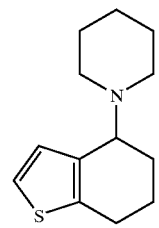

IC180

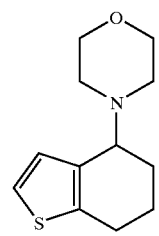

IC194

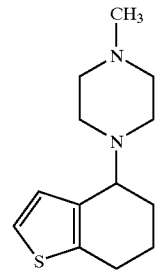

IC193

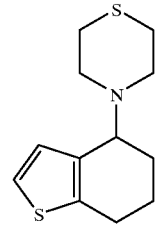

IC209

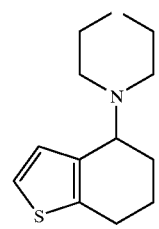

IC241
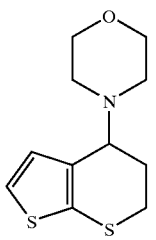

IC140
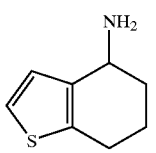

IC237
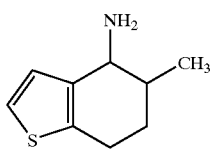

IC242
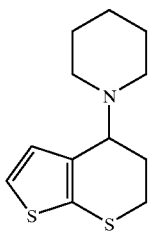

A particularly preferred compound of formula (II) is the compound IC023 represented by the following formula:

IC023
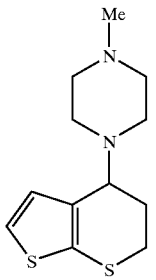

Another particularly preferred compound of formula (II) is the compound IC180 represented by the following formula:

IC180
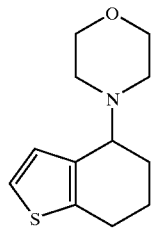

The invention relates even more particularly to the compounds as defined above, with the following formula (III):

(III)

in which $R_3$, $R_4$ and $R_5$ have the meanings stated above.

Particularly preferred compounds of formula (III) are those represented by the following formulae:

IC146

IC178

IC2-16
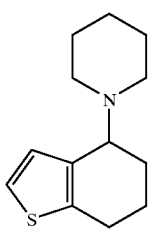

The invention relates even more particularly to the compounds as defined above, with the following formula (IV):

(IV)

in which $R_3$, $R_4$, and $R_5$ have the meanings stated above.

Particularly preferred compounds of formula (IV) are those represented by the following formulae:

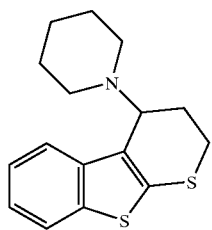
IC249

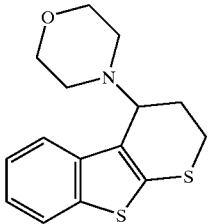
IC2-19

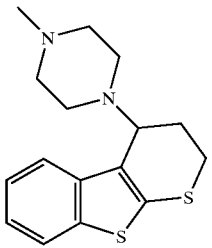
IC2-21

The invention relates even more particularly to the compounds as defined above, with the following formula (V):

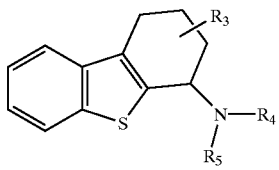
(V)

Particularly preferred compounds of formula (V) are those represented by the following formulae:

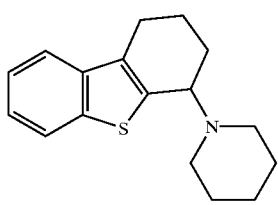
IC207

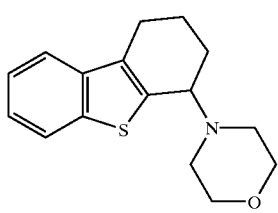
IC219

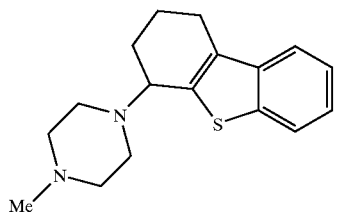
IC2-38

The invention also relates to the use of at least one compound with the following general formula

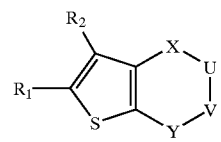

in which:
  $R_1$ and $R_2$ are as defined above,
  X, Y, U and V, independently of one another, represent $CHR_3$, $R_3$ being as defined above, or a heteroatom such as a sulphur atom S, at least one of X, Y, U or V represents a group with the formula

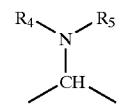

in which $R_4$ and $R_5$ are as defined above,
for the preparation of a drug (neuroprotector) intended for the treatment of pathologies connected with abnormally high concentrations of extracellular glutamate.

The invention relates more particularly to the aforementioned use of compounds of formula (I) described above in which one at least of X or Y represents a group with the formula

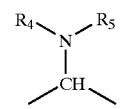

in which $R_4$ and $R_5$ are as defined above, and especially the compounds described above of formulae (II), (III), (IV) and (V).

Among the pathologies that can be treated within the scope of the present invention, we may mention:
  acute pathological cases of neuron death such as
    ischaemias, especially those caused by cerebral haemorrhages, blood clots, cerebral vascular injuries such as those arising from heart attacks, or arterial spasms caused by a lack of supply of nutrients to the cells,
    traumatisms of the central nervous system in general, especially those of the spinal cord,
    stroke,
    the effects of exogenous poisons on the CNS,
  chronic neurodegenerative disorders such as:
    Alzheimer's disease,
    Parkinson's disease,
    Huntington's chorea,
    amyotrophic lateral sclerosis,
    the effects of ageing.

The invention also relates to any pharmaceutical composition, containing, as active principle, at least one compound such as described above, if necessary in the form of a salt, especially a hydrochloride, in conjunction with a pharmaceutically acceptable vehicle.

The aforementioned pharmaceutical compositions of the invention are preferably in a form that can be administered by the oral, parenteral or rectal route.

The doses of active principle in the said pharmaceutical compositions are preferably between about 0.1 to about 50 mg/kg/day.

The invention relates more particularly to any pharmaceutical composition such as described above, characterized in that:
- the dosage of the forms that can be administered parenterally in the treatment of acute diseases is between. 0.1 to 10 mg/kg/day by the intravenous route, and between 0.5 to 30 mg/kg/day by the intramuscular route,
- the dosage of the forms that can be administered by the oral or parenteral route in the treatment of chronic diseases is between, respectively, 5 to 50 mg/kg/day per os, and between 0.1 to 5 mg/kg/day by the intramuscular route.

Preferably, the aforementioned compounds of the invention can be obtained by employing the following methods of preparation:

1) the compounds of formula (II) in which $R_4$ and $R_5$ are as defined above, Y represents $CH_2$ and $R_3$ represents a hydrogen atom, namely compounds of the following formula (IIa):

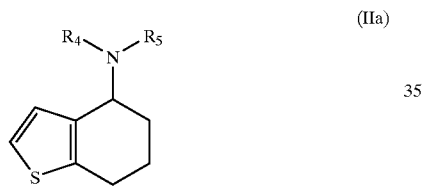
(IIa)

are obtained by a method comprising the following stages:

reaction of thiophene and succinic anhydride, preferably in the presence of $AlCl_3$ with stirring for about 5 hours at room temperature, which leads to production of compound (1), according to the following reaction scheme:

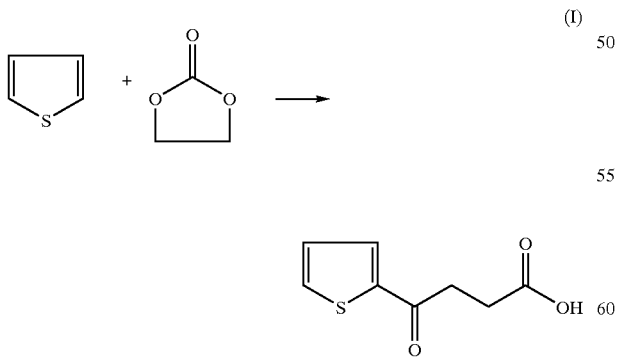
(1)

treatment of compound (1) thus obtained with hydrazine in the presence of potash with stirring preferably for about 7 hours at 190° C., which leads to production of the following compound (2):

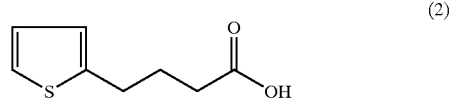
(2)

cyclization of compound (2) thus obtained by treatment of the latter with acetic anhydride in the presence of orthophosphoric acid preferably for about 2 hours 30 minutes at 120° C., which leads to production of the following compound (3):

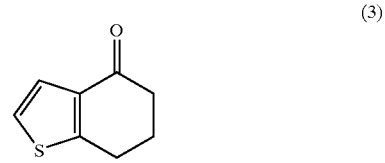
(3)

reaction between compound (3) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIa), 2) compounds of formula (II) in which $R_4$ and $R_5$ are as defined above, Y represents a sulphur atom S, and $R_3$ represents a hydrogen atom, namely compounds of the following formula (IIb):

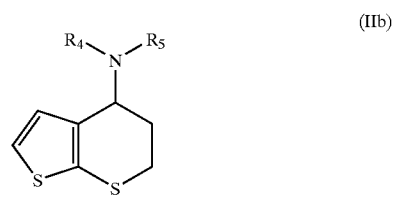
(IIb)

are obtained by a method comprising the following stages:

reaction of thiophene and sulphur, preferably in the presence of n-butyllithium with stirring for about 1 hour at 0–5° C., which leads to production of the following compound (4):

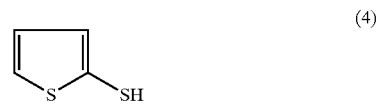
(4)

treatment of compound (4) thus obtained with 3-bromopropanoic acid, preferably with stirring for about 24 hours at room temperature, which leads to production of the following compound (5):

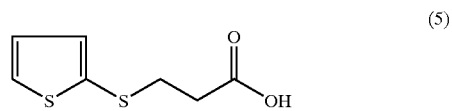
(5)

cyclization of compound (5) thus obtained by treatment of the latter with trifluoroacetic anhydride preferably for about 3 hours 30 minutes at 36° C., which leads to production of the following compound (6):

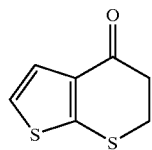
(6)

reaction between compound (6) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIb), 3) compounds of formula (II) in which $R_4$ and $R_5$ are as defined above, Y represents $CH_2$ or a sulphur atom S, and $R_3$ represents an alkyl group with 1 to 5 carbon atoms, especially a methyl group, namely compounds of the following formula (IIc; Y=$CH_2$), and compounds of the following formula (IId; Y=S):

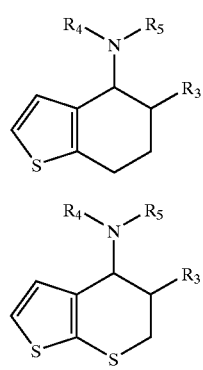
(IIc)

(IId)

are obtained respectively by methods a) and b) comprising the following stages a)—treatment of the aforementioned compound (3) with an alkyl halogen of formula $XR_3$ in which X represents a halogen atom, especially an atom of iodine, and $R_3$ is as defined above, with stirring, preferably for about 2 hours at room temperature, which leads to production of the following compound (7):

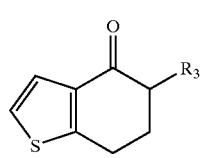
(7)

reaction between compound (7) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIc), b)—treatment of the aforementioned compound (6) with an alkyl halogen of formula $XR_3$ in which X represents a halogen atom, especially an atom of iodine, and $R_3$ is as defined above, with stirring, preferably for about 2 hours at room temperature, which leads to production of the following compound (8):

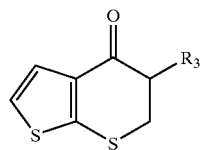
(8)

reaction between compound (8) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IId);

4) compounds of formula (III) in which $R_4$ and $R_5$ are as defined above, and $R_3$ represents a hydrogen atom, namely compounds with the following formula (IIIa);

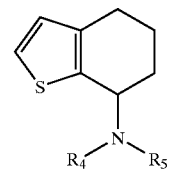
(IIIa)

are obtained by:

treatment of the aforementioned compound (3) with hydrazine in the presence of potash with stirring, preferably for about 8 hours at 190° C., then by hydrolysis at room temperature, which leads to production of the following compound (9):

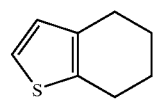
(9)

treatment of compound (9) thus obtained with cerium IV nitrate, with stirring, preferably for about 2 hours at −15° C. then about another 2 hours at room temperature, which leads to production of the following compound (10):

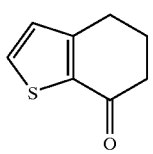
(10)

reaction between the compound (10) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIIa), 5) compounds of formula (III) in which $R_4$ and $R_5$ are as defined above, and $R_3$ represents an alkyl group with 1 to 5 carbon atoms, especially a methyl group, namely compounds of the following formula (IIIb), and compounds of the following formula (IIc):

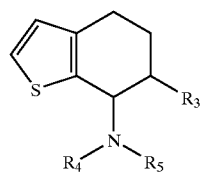
(IIIb)

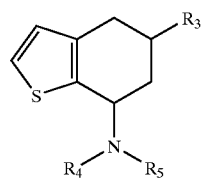
(IIIc)

are obtained by:
a)—treatment of the aforementioned compound (10) with an alkyl halogen of formula $XR_3$ in which X represents a halogen atom, especially an atom of iodine, and $R_3$ is as defined above, with stirring, preferably for about 2 hours at room temperature, which leads to production of the following compound (11):

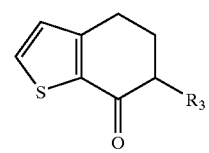
(11)

reaction between compound (11) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIIb), b)—treatment of the aforementioned compound (7) with hydrazine in the presence of potash with stirring, preferably for about 8 hours at 190° C., then by hydrolysis at room temperature, which leads to production of the following compound (12):

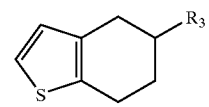
(12)

treatment of compound (12) thus obtained with cerium IV nitrate with stirring, preferably for about 2 hours at —15° C. then for about another 2 hours at room temperature, which leads to production of the following compound (13):

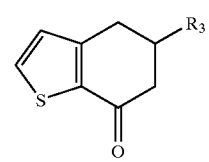
(13)

reaction between compound (13) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IIIc), 6) compounds of formula (I) in which $R_4$ and $R_5$ are as defined above, and $R_3$ represents a hydrogen atom, namely compounds of the following formula (IVa):

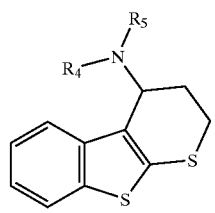
(IVa)

are obtained by:
reaction of benzothiophene and sulphur, preferably in the presence of n-butyllithium with stirring for about 1 hour at 0–5° C., which leads to production of the following compound (14):

(14)

treatment of the compound (14) thus obtained with 3-bromopropanoic acid, preferably with stirring for about 24 hours at room temperature, which leads to production of the following compound (15):

(15)

cyclization of compound (15) thus obtained by treatment of the latter with trifluoroacetic anhydride preferably for about 3 hours 30 minutes at 36° C., which leads to production of the following compound (16):

(16)

reaction between compound (16) thus obtained and a compound of formula $HNR_4R_5$, in which $R_4$ and $R_5$ are as defined above, preferably in the form of a salt of acetic (or hydrochloric) acid for about 5 days at about 80° C., which leads to production of compounds of the aforementioned formula (IVa), 7) compounds of formula (V) in which $R_4$ and $R_5$ are as defined above, and $R_3$ represents a hydrogen atom, namely compounds of the following formula (Va):

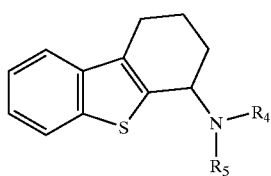

(Va)

are obtained by:
reaction of benzothiophene and succinic anhydride, preferably in the presence of AlCl$_3$ with stirring for about 5 hours at room temperature, which leads to production of compound (17), according to the following reaction scheme:

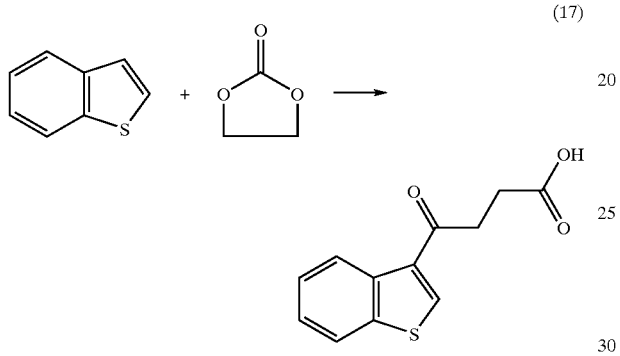

(17)

treatment of compound (17) thus obtained with hydrazine in the presence of potash with stirring preferably for about 6 hours at 180° C., which leads to production of the following compound (18):

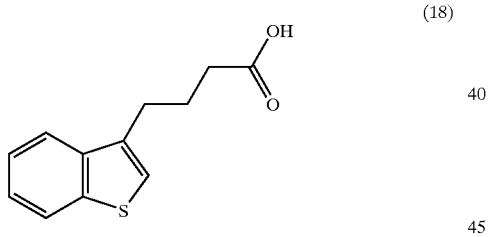

(18)

cyclization of compound (18) thus obtained by treatment of the latter with acetic anhydride in the presence of orthophosphoric acid preferably for about 7 hours at 130° C., which leads to production of the following compound (19):

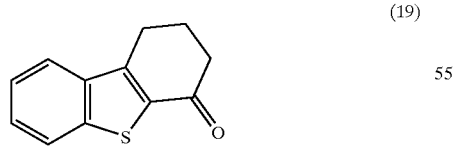

(19)

reaction between compound (19) thus obtained and a compound of formula HNR$_4$R$_5$, in which R$_4$ and R$_5$ are as defined above, preferably in the form of a salt of acetic (or hydrochloric) acid for about 5 days at about 80° C., which leads to production of compounds of the aforementioned formula (Va), 8) compounds of formula (IV) in which R$_4$ and R$_5$ are as defined above, and R$_3$ represents an alkyl group with 1 to 5 carbon atoms, especially a methyl group, namely the compounds of the following formula (IVb):

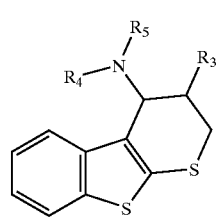

(IVb)

are obtained by:
treatment of the aforementioned compound (16) with an alkyl halogen of formula XR$_3$ in which X represents a halogen atom, especially an atom of iodine, and R$_3$ is as defined above, with stirring, preferably for about 2 hours at room temperature, which leads to production of the following compound (20):

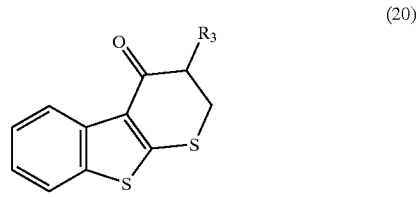

(20)

reaction between compound (20) thus obtained and a compound of HNR$_4$R$_5$, in which R$_4$ and R$_5$ are as defined above, preferably in the form of a salt of acetic (or hydrochloric) acid for about 5 days at about 80° C., which leads to production of compounds of the aforementioned formula (IVb), 9) compounds of formula (V) in which R$_4$ and R$_5$ are as defined above, and R$_3$ represents an alkyl group with 1 to 5 carbon atoms, especially a methyl group, namely compounds of the following formula (Vb):

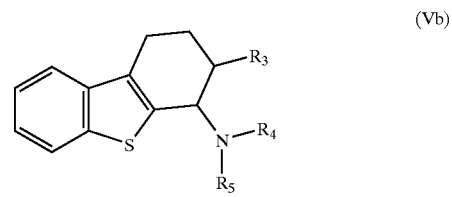

(Vb)

are obtained by:
treatment of the aforementioned compound (19) with an alkyl halogen of formula XR$_3$ in which X represents a halogen atom, especially an atom of iodine, and R$_3$ is as defined above, preferably for about 2 hours at room temperature, which leads to production of the following compound (21):

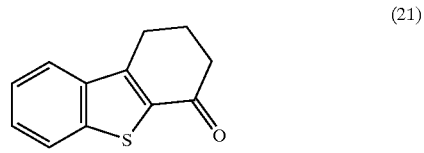

(21)

reaction between compound (21) thus obtained and a compound of formula HNR$_4$R$_5$, in which R$_4$ and R$_5$ are as defined above, preferably in the form of a salt of acetic (or hydrochloric) acid for about 5 days at about 80° C., which leads to production of compounds of the aforementioned formula (Vb).

The invention will be further illustrated by means of the detailed description that follows, of examples of synthesis of compounds of the invention, and of investigation of their ability to capture OH• radicals, and of their effects on the recapture of glutamate by astrocytes.

α) examples of synthesis of compounds of the invention

The end products were obtained starting from the corresponding ketone derivatives by a reaction of reductive amination. That is why production of the various ketones required is dealt with before the actual reactions of amination.

I-Synthesis of ketone derivatives
A) oxo-4-tetrahydro-4,5,6,7-benzothiophene
  a) 4-(2-thienyl)-4-keto-butyric acid

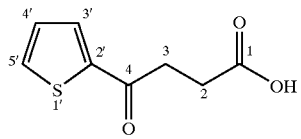

3.57 g (0.036 mol) of succinic anhydride, 10.46 g (0.036 mol) of $AlCl_3$ and 35 ml of nitrobenzene are placed in a three-necked flask under nitrogen atmosphere, equipped with a magnetic stirrer and cooled on an ice bath. 2.85 ml (0.036 mol) of thiophene dissolved in 17 ml of nitrobenzene is then added a drop at a time. The yellow medium turns a uniform brown during addition. Stirring is maintained for 5 h at room temperature. The medium cooled on the ice bath is hydrolysed with 25 ml of HCl 36% diluted in 20 ml of ice water. The nitrobenzene is carried over with the steam and the residue that remains is absorbed in a solution of $Na_2CO_3$. Repeating steam distillation removes the volatile products and the remaining solvent. The aqueous phase is acidified then extracted with ether which is dried over $MgSO_4$ and concentrated. The acid is obtained in the form of 3.6 g of bright pale-yellow flakes after recrystallization in water. Yield=55%.

NMR $^1H$ ($CDCl_3$) δ ppm: 7.77 (d, 1H, H5'); 7.66 (d, 1H, H3'); 7.15 (m, 1H, H4'); 3.28 (t, 2H, H3); 2.82 (t, 2H, H2).

NMR $^{13}C$ ($CDCl_3$) δ ppm: 192.27 (C4); 180 (C1); 144.54 (C2'); 133.7 (C3'); 132.04 (C5'); 128.071 (C4'); 33.58 (C3); 27.87 (C2).

b) 4-(2-thienyl)-butyric acid

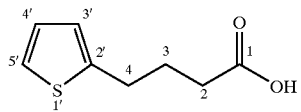

3.6 g (0.019 mol) of 4-(2-thienyl)-4-keto-butyric acid, 2.74 ml (0.07 mol) of hydrazine 98%, 3.69 g (0.066 mol) of potash and 42 ml of diethylene glycol are placed in a two-necked flask equipped with a magnetic stirrer. The medium is heated for 7 h at 190° C. The medium is a clear uniform yellow. When it has cooled to room temperature it is hydrolysed with 200 ml of water. The diethylene glycol is extracted with 5 times 100 ml of ether. The aqueous phase is then acidified to pH 1 and extracted. The acid is absorbed in a solution of soda 5% washed with ether then acidified and absorbed for the last time in ether which is dried over $MgSO_4$ and concentrated. 2.74 g of a clear yellow oil is obtained. Yield=85%.

NMR $^1H$ ($CDCl_3$) δ ppm: 7.15 (d, 1H, H3'); 6.96 (t, 1H, H4'); 6.84 (d, 1H, H5'); 2.93 (t, 2H, H2); 2.45 (t, 1H, H4); 2.04 (q, 2H, H3).

NMR $^{13}C$ (CDCl3) δ ppm: 143.63 (C1); 127.27 (C3'); 124.84 (C5'); 123 (C4'); 33.3 (C2); 28.48 (C4); 26.06 (C3).

c) oxo-4 tetrahydro-4,5,6,7-benzothiophene

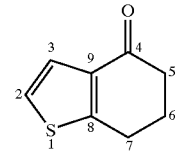

1) 2.74 g (0.023 mol) of 4-(2-thienyl)-butyric acid dissolved in 3.91 ml of acetic anhydride in the presence of 0.08 ml of orthophosphoric acid at 85% are placed in a two-necked flask equipped with a magnetic stirrer. The uniform reddish-brown medium is heated at 120° C. for 2 h30. After cooling on an ice bath, the medium is hydrolysed with 20 ml of water. The aqueous phase is alkalized with a solution of soda at 20% and is extracted with 3 times 12 ml of $CH_2Cl_2$. The organic phase is rinsed with water to pH 7, dried over $MgSO_4$ and concentrated. 2.23 g of white solid recrystallised in petroleum ether is obtained. Yield=65%

2) 1 g (0.006 mol) of 4-(2-thienyl)-butyric acid dissolved in 5 ml of anhydrous ether is placed in a three-necked flask under nitrogen atmosphere, equipped with a magnetic stirrer and funnel. A solution of 0.51 ml (0.007 mol) of thionyl chloride dissolved in 1 ml of anhydrous ether is then added dropwise. The orange-brown medium is refluxed for 4 h. The ether and the excess thionyl chloride are distilled. The residue is absorbed in a few milliliters of $CS_2$ and then cooled on an ice bath. 0.67 ml (0.006 mol) of $SnCl_4$ dissolved in 5 ml of $CS_2$ is added slowly. The medium, which has turned a uniform black, is stirred vigorously at room temperature over night. The reddish-black medium is decomposed on ice and 20 ml of HCl 5%. The $CS_2$ is concentrated then the aqueous phase is extracted with 3 times 10 ml of ether. The organic phase is washed with soda 5%, with water, dried over MgSO4 and concentrated. 550 mg of white solid recrystallised in petroleum ether is obtained. Yield=62%

NMR $^1H$ (CDCl3) δ ppm: 7.24–7.21 (d, 1H, d, 1H, H2–H3) J23=0.34; 3.04 (t, 1H, H5); 2.57 (m, 1H, H7); 2.22 (m, 1H, H6).

NMR $^{13}C$ (CDCl3) δ ppm: 193.33 (C4); 155.75 (C9); 136.97 (C8); 124.8 (C2); 122.4 (C3); 38.18 (C7); 25.45 (C5); 24.24 (C6).

B) oxo-7-tetrahydro-4,5,6,7-benzothiophene
  a) tetrahydro-4,5,6,7 benzothiophene

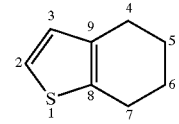

1.1 g (0.007 mol) of oxo-4-tetrahydro-4,5,6,7 benzothiophene, 0.96 ml (0.028 mol) of hydrazine 98%, and 1.36 g (0.024 mol) of potash dissolved in 20 ml of diethylene glycol are placed in a three-necked flask equipped with a magnetic stirrer. The medium is kept at 190° C. for 8 h. After cooling to room temperature, the medium is hydrolysed with 100 ml of water. The aqueous phase is extracted with ether which is washed several times with small amounts of water, dried over $MgSO_4$ and concentrated. 950 mg of transparent oil is obtained. Yield=95%

NMR $^1$H (CDCl3) δ ppm: 7.03–6.74 (d, 1H, d, 1H, H2–H3) J23=0.29; 2.75–2.63 (t, 2H, t, 2H, H4–H7); 1.82 (m, 4H, H5–H6).

NMR $^{13}$C (CDCl3) δ ppm: 129.18 (C9), 125.98 (C8), 123.31 (C3), 119.62 (C2), 25.49 (C4), 24.87 (C7), 23.63 (C5), 22.88 (C6).

b) oxo-7-tetrahydro-4,5,6,7-benzothiophene

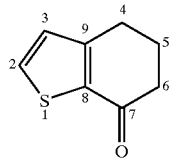

1 g (0.0072 mol) of tetrahydro-4,5,6,7-benzothiophene dissolved in 35 ml of AcOH/H$_2$O mixture (50/50) is placed in a three-necked flask equipped with a magnetic stirrer and funnel, cooled to −15° C. 15.88 g (0.03 mol) of cerium IV nitrate dissolved in 70 ml of AcOH/H$_2$O (50/50) is added dropwise. Throughout addition, the medium must remain pale yellow (or even slightly orange). After 2 h of stirring at −15° C. it is left to return to room temperature and then stirring is continued for a further 2 h. The medium is then deep yellow. The medium is diluted with 50 ml of water and then extracted with ether. The organic phase is washed with soda 5%, with water, dried over MgSO$_4$ and concentrated. The oil obtained is chromatographed on silica, eluent EP/Et$_2$O (60/40), giving 800 mg of yellow oil. Yield=72%.

NMR $^1$H (CDCl3) δ ppm: 7.62–6.98 (d, 1H, d, 1H, H2–H3) J23=0.63; 2.89 (t, 2H, H6); 2.62 (t, 2H, H4); 2.18 (q, 2H, H5).

NMR $^{13}$C (CDCl3) δ ppm: 170.8 (C7); 153.13 (C8); 136.27 (C9); 133.702 (C2); 128.152 (C3); 38.09 (C6); 25.87 (C4); 24.26 (C5).

C) oxo-4-methyl-5-tetrahydro-4,5,6,7-benzothiophene

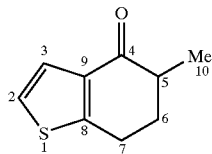

3.68 ml (0.026 mol) of diisopropylamine dissolved in 20 ml of anhydrous THF is placed in a three-necked flask under nitrogen atmosphere, equipped with a magnetic stirrer and a dropping funnel. 16.42 ml (0.026 mol) of n-butylllithium at 1.6 M in hexane is added dropwise. Once addition is completed, the medium is stirred for half an hour at room temperature. The medium is cooled to −80° C. then 4 g (0.026 mol) of oxo-4-tetrahydro-4,5,6,7-benzothiophene dissolved in 3 ml of THF is added. The temperature is raised slowly to −30° C. (maintained for about ten minutes). The medium is then cooled to −78° C. for making a single addition of 4.9 ml (0.078 mol) of methyl iodide. The medium is stirred for 2 h at room temperature. It is hydrolysed with 30 ml of ice water. The THF is concentrated then the aqueous phase is extracted with ether which is dried over MgSO$_4$ and concentrated. 4.09 g of transparent oil is obtained. The oil is chromatographed by preparative HPLC on 250 g of silica 0.04 mm-eluent:heptane. A 1 g fraction of a mixture of mono- and di-methylated products is isolated followed by a 2.3 g fraction of pure monomethylated product. Finally the starting ketone is recovered. Degree of conversion=72%. Yield of monomethylated product isolated=52%.

NMR $^1$H (CDCl3) δ ppm: 7.38–7.06 (2d, 2H, H2–H3) J23=0.32; 3.07 (m, 2H, H7); 2.61–2.3–2.08 (3m, 3H, H5–H6); 1.26 (d, 3H, Me).

NMR $^{13}$C (CDCl3) δ ppm: 196.5 (C4); 155.9 (C8); 136.4 (C9); 124.33 (C3); 123.079 (C2); 41.35 (C5); 32.51 (C7); 24.53 (C6); 14.83 (C10).

D) oxo-4-tetrahydro-4,5,6,7-thio-7-benzothiophene a) S-(2'-thiophenyl)-3-thio-propanoic acid

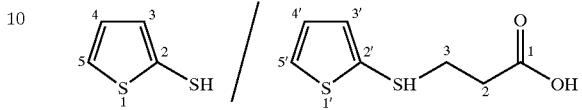

6.7 ml (0.083 mol) of thiophene dissolved in 40 ml of THF is placed in a three-necked flask under inert atmosphere, equipped with a magnetic stirrer, with a dropping funnel and cooled to 0° C. by means of a refrigerating machine. 49 ml (0.079 mol) of n-butyllithium 1.6M in hexane is added dropwise in such a way that the temperature remains below 20° C. After stirring for one hour at 0–5° C., 2.51 g (0.079 mol) of sulphur dried beforehand in a stove is added in 20 min; it is stirred for 2 h, then the medium is hydrolysed with 16 ml of water purged with nitrogen; the temperature remains below 10° C. and the medium is deep yellow. In another two-necked flask a solution of 4.8 g of K$_2$CO$_3$ dissolved in 16 ml of water is purged with nitrogen. 10.94 g of 3-bromo-propanoic acid is added using a spatula, and the medium is stirred until it is clear. This solution is then added dropwise to the first medium, keeping the temperature below 5° C.; the medium, which has turned green, is stirred for 24 h at room temperature. After concentrating the THF, the aqueous phase is washed with 10 ml of toluene, acidified with 16 ml of HCl 6N then extracted with 3 times 40 ml of toluene. The organic phase is concentrated; any remaining water is removed by a second azeotropic distillation effected with 20 ml of toluene. 13.5 g of yellow oil is obtained. Yield=86%.

NMR $^1$H (CDCl3) δ ppm: 9.61 (s, 1H, acid); 7.39 (d, 1H, H5'); 7.18 (d, 1H, H3'); 7.00 (q, 1H, H4); 3.02 (t, 1H, H3); 2.68 (t, 1H, H2).

NMR $^{13}$C (CDCl3) δ ppm: 177.84 (C1); 134.82 (C5'); 132.66 (C2'); 130.09 (C3'); 127.62 (C4'); 34.22 (C3); 33.14 (C2).

b) oxo-4-tetrahydro-4,5,6,7-thio-7-benzothiophene

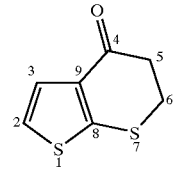

13.5 g (0.072 mol) of S-(2'-thiophenyl)-3-thio-propanoic acid is placed in a two-necked flask under nitrogen, equipped with a magnetic stirrer, and 11 ml of trifluoroacetic anhydride is slowly added. The medium, which has turned black, is held for 3 h30 at 36° C. The solution is cooled on an ice bath, hydrolysed with 50 ml of water and then alkalized to pH9. The aqueous phase is extracted with toluene which in its turn is washed with water and then concentrated. The product obtained is quickly chromatographed on silica-eluent EP/Et$_2$O (50/50). 10 g of a pale yellow solid is obtained, which when recrystallized in petroleum ether gives 8.5 g of white crystals. (During recrystallization some traces of oxo-7 product are eliminated). Yield=70%.

NMR $^1$H (CDCl3) δ ppm: 7.46–7.02 (2d, 2H, H2–H3); 3.37 (t, 1H, H6); 2.87 (t, 2H, H4).

NMR $^{13}$C (CDCl3) δ ppm: 188.96 (C4), 150.91 (C9), 135.00 (C8), 126.08 (C3), 121.81 (C2), 38.16 (C6), 30.04 (C5).

E) Synthesis of oxo-1-tetrahydro-1,2,3,4-thio-9-fluorene a) 4-oxo-4-(3'-benzothiophenyl)-butyric acid

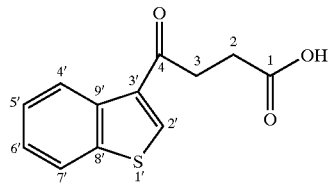

16 g (0.119 mol) of benzothiophene and 11.9 g (0.119 mol) of succinic anhydride dissolved in 250 ml of dichloromethane are placed in a three-necked flask under a nitrogen atmosphere, equipped with a magnetic stirrer and cooled on an ice bath. The medium is transparent and heterogeneous. 32 g (0.24 mol) of AlCl$_3$ is introduced in 40 minutes; the medium is then a uniform reddish-black, and very thick. After introduction, the medium is stirred for 1 h at 0° C. and then over night at room temperature. The medium is hydrolysed with 30 ml HCl 36% diluted in 40 ml of ice. Stirring becomes very difficult. The organic phase is washed with water then extracted with a solution of sodium carbonate. The aqueous phase is heated in the presence of activated carbon, filtered, then acidified and extracted with dichloromethane. This last phase is dried over MgSO$_4$ and concentrated. 18 g of very thick yellow oil which crystallizes in the cold is obtained. The main product is the desired product but one third is alkylated in position 2' of the benzothiophene; the two products will be separated later on. Overall yield=65%.

NMR $^1$H (Acetone d6) δ ppm: 8.73 (d, 1H, H4'); 7.96 (d, 1H, H7'); 7.45 (m, 2H, H5'–H6'); 3.36 (t, 2H, H3); 2.76 (t, 2H, H2).

NMR $^{13}$C (Acetone d6) δ ppm: 194.9 (C4), 174.57 (C1), 140.095 (C9); 138.72 (C8); 137.61 (C2); 135.49 (C3); 126.42–126.17–126.14 (C4–C5–C7); 123.28 (C6); 35.32 (C11); 28.30 (C12).

b) 4-(3'-benzothiophenyl)-butyric acid

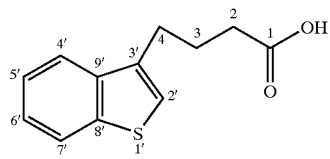

18 g (0.077 mol) of 4-oxo-4-(3'-benzothiophenyl)-butyric acid, 11.12 ml (0.3 mol) of hydrazine 98%, and 16.8 g (0.3 mol) of potash dissolved in 150 ml of diethylene glycol are placed in a two-necked flask equipped with a magnetic stirrer. The medium is heated for 6 h at 180° C. The medium is absorbed in water, washed with ether then acidified to pH 1 and extracted with ether. The organic phase is washed with water, dried over MgSO$_4$ and concentrated. 11.11 g of orange oil is obtained. Yield=60%.

NMR $^1$H (CDCl3) δ ppm: 7.76–7.67 (2d, 2H, H4'–H7'); 7.35 (m, 3H, H2'–H5'–H6'); 3.02 (t, 2H, H2); 2.49 (t, 2H, H4); 2.14 (q, 2H, H3).

NMR $^{13}$C (CDCl3) δ ppm: 179.14 (C1); 144.8 (C9'); 140.04 (C8'); 139.3 (C3'); 124.14–123.59–122.87–122.12–121.18 (C2', C4', C5', C6'.C7').

c) oxo-1-tetrahydro-1,2,3,4 thio-9-fluorene

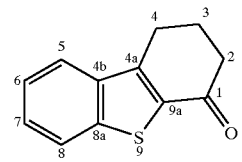

1) 11.11 g (0.05 mol) of 4-(3-benzothiophenyl)-butyric acid, 8.65 g of acetic anhydride and 0.17 ml of orthophosphoric acid at 85% are placed in a two-necked flask under a nitrogen atmosphere, equipped with a magnetic stirrer. The medium is kept at 130° C. for 7 h. It is hydrolysed with 10 ml of ice water and the ketone is extracted with ether. The organic phase is washed with soda 10% and then with water to pH 7, dried over MgSO$_4$ and concentrated. 10.37 g of a red solid is obtained.

This solid is quickly chromatographed on silica and eluted with a EP/Et$_2$O mixture (60/40). 9 g of a white solid containing 25% of oxo-4 derivative and 75% of oxo-1 derivative is obtained. Yield=60%. The pure product is obtained by chromatography on silica, eluent EP/Acetone (9/1), then recrystallization of the fraction enriched with oxo-1 derivative in ether.

2) 5.7 g (0.026 mol) of 4-(3-benzothiophenyl) butyric acid in 10 ml of toluene is placed in a two-necked flask under a nitrogen atmosphere, equipped with a magnetic stirrer. 6.1 ml (0.028 mol) of trifluoroacetic anhydride is added dropwise. The medium turns black. After 24 h of stirring at room temperature the reaction is stopped. After treatment as described above, 5.2 g of a reddish solid is obtained, then after quick chromatography, 5 g of a white solid containing one third of oxo-4 derivative and ⅔ of oxo-1 derivative. Yield=65%

NMR $^1$H (CDCl3) δ ppm: 8.61 (d, 1H, H5); 7.56 (d, 1H, H8); 7.31 (m, 2H, H6–H7); 2.85 (t, 2H, H4); 2.46 (t, 2H, H2); 2.03 (m, 2H, H3).

NMR $^{13}$C (CDCl3) δ ppm: 193.18 (C1); 159.99 (C9a); 137.17 (C4b); 137 (C8a); 129.48 (C4a); 126.26–123.8–123.1–119.9 (C5–C6–C7–C8); 35.52 (C4); 26.14 (C2); 24.00 (C11).

F) oxo-4-tetrahydro-1,2,3,4-dithio-1,9-fluorene a) S-(2'-benzothiophenyl)-3-thio-propanoic acid

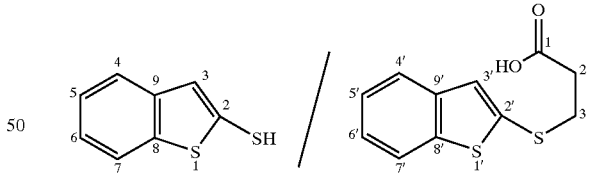

16.66 g (0.124 mol) of benzothiophene dissolved in 15 ml of THF is placed in a three-necked flask under inert atmosphere, equipped with a magnetic stirrer, with a dropping funnel and cooled to −20° C. by means of a refrigerating machine. 77.8 ml (0.124 mol) of n-butyllithium 1.6M in hexane is added dropwise, keeping the temperature between −25° C. and −20° C. At the end of addition, the medium is orange, oily and heterogenous; it is placed under reflux. After 2 h00, reflux is stopped and the lithium is cooled to −20° C. 3.96 g (0.124 mol) of powdered sulphur, previously dried in the stove, is introduced a spatula at a time, then stirring is continued for a further three hours at 0° C.−5° C. before hydrolysis, which is effected with 24 ml of nitrogen-purged water. In another two-necked flask, a solution of 7.18 g of $K_2CO_3$ dissolved in 24 ml of water is purged with nitrogen. 16.36 g of 3-bromo-propanoic acid is added one spatula at a time, and is stirred until the medium is clear. This solution is then added dropwise to the first medium which is at 0° C., keeping the temperature below 5° C.; the two-phase red medium is stirred for 16 h00 at room temperature. After concentrating the THF, the aqueous phase is washed with a few milliliters of toluene and is then alkalized with HCl 6N before being extracted with toluene. The organic phase is concentrated (any remaining water is eliminated azeotropically with a few extra milliliters of toluene). 29.35 g (0.123 mol) of a pale yellow solid is obtained. Yield is quantitative.

NMR $^1H$ (CDCl3) δ ppm: 7.74 (m, 2H, H4'–H7'), 7.36 (m, 3H, H3'–H5'–H6'), 3.14 (t, 1H, H3), 2.74 (t, 1H, H2).

NMR $^{13}C$ (CDCl3) δ ppm: 177.34 (C1), 141.98 (C9'), 139.53 (C8'), 135.11 (C2'), 129.90 (C3'), 124.64 (C5'), 124.47 (C6'), 123.22 (C7'), 121.86 (C4'), 32.24 (C3), 31.92 (C2).

b) oxo-4-tetrahydro-1,2,3,4-dithio-1,9-fluorene

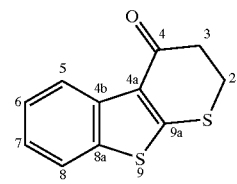

In a three-necked flask under inert atmosphere, equipped with a magnetic stirrer and a dropping funnel, 40 ml of trifluoroacetic anhydride is added dropwise to 29.35 g (0.123 mol) of S-(2'-benzothiophenyl) 3-thio-propanoic acid dissolved in 90 ml of toluene. The medium is kept at 40° C. for 3 h30, then cooled on an ice bath, hydrolysed with 50 ml of water, and then the solution is alkalized to pH 9. The aqueous phase is extracted with toluene which in its turn is washed with water and then concentrated. 20 g of a pale yellow solid containing a few traces of 1-oxo product is obtained (3-alkylation on benzothiophene). Yield=75%. The by-product is eliminated by recrystallization in ethyl acetate.

NMR $^1H$ (CDCl3) δ ppm: 8.65 (t, 1H, H8), 7.68 (t, 1H, H5), 7.42 (m, 2H, H6–H7), 3.42 (t, 2H, H2), 2.97 (t, 2H, H3).

NMR $^{13}C$ (CDCl3) δ ppm: 189.30 (C4), 157.1 (C4a), 136.94 (C4b), 136.05 (C8a), 127.32 (C9a), 127.32–125.96 (C6–C7), 124.82–121.0 (C5–C8), 39.04 (C3), 29.82 (C2).

II) Synthesis of aminated derivatives
General procedure

For the piperidine, N-methyl piperazine, morpholine and thiomorpholine derivatives, the corresponding salts of acetic acid are formed first; 1 eq of amine is placed in anhydrous ether and one equivalent of acetic acid (2 eq in the case of N-methyl piperazine) dissolved in ether is added dropwise. (Formation of the salt is carried out under nitrogen in the case of thiomorpholine). After stirring for one hour, the ether is concentrated and the salt is dried over night at 40° C. under vacuum.

In the case of 4-hydroxypiperazine, the hydrochloride is formed in ethyl chloride 3N, concentrated and dried over night at 40° C. under vacuum.

1 eq of ketone and 10 eq of amine in the form of salt of acetic (or hydrochloric) acid dissolved in 20 volumes of MeOH are placed in a two-necked flask under nitrogen, equipped with a magnetic stirrer and an actigel trap. 1.5 eq of $NaBH_3CN$ is added, and the medium is heated for 5 days at 80° C. The medium is hydrolysed with ice water, the methanol is concentrated and then the alkaline aqueous phase is extracted with ether. The amine is absorbed in acidified water (to pH1), rinsed with ether then alkalized (pH 9) before being extracted finally with ether, which is then dried over $MgSO_4$ and concentrated. The derivatives are purified by chromatography on neutral alumina with $EP/Et_2O$ (60/40) eluent. Conversion to the hydrochloride is effected by dissolving the amine in a minimum of ether and dropwise addition in ethyl chloride 3N.

A) piperidino-4-tetrahydro-4,5,6,7-benzothiophene (IC023)

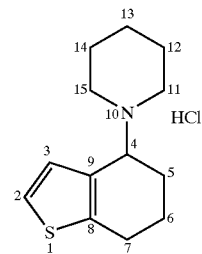

The amine was chromatographed on neutral alumina; eluent petroleum ether/ether (50/50). Yield=73%.
Base
NMR $^1H$ (CDCl3) δ ppm: 7.10–7.08 (2d, 2H, H2–H3) J23=0.073 ppm; 3.79 (t, 1H, H4); 2.77 to 0.94 (m, 16H, alkyls).

NMR $^{13}C$ (CDCl3) δ ppm: 138.32 (C9); 137.27 (C8); 127.34 (C3); 121.07 (C2); 61.9 (C4); 49.66 (C10–C14); 26.72–25.05–24.94–22.88 (C5–C7–C12–C13–C14); 21.21 (C6)

GC-MS: 90° C./10° min/250° C.; 13.74 min; 221/193/178/137/136/86.
Hydrochloride:
NMR $^1H$ (CDCl3) δ ppm: 12.072 (s, 1H, ammonium); 7.51–7.48 (2d, 2H, H2–H3) J23=0.81; 4.6 (t, 1H, H4); 3.47 to 1.42 (m, 16H, alkyls).

NMR $^{13}C$ (CDCl3) δ ppm: 142.28 (C9); 127.72 (C3); 127.63 (C8); 123.63 (C2); 61.38 (C4); 51.66–47.39 (C11–C15); 24.46–22.77–22.36–22.26–22.01 (C5–C6–C7–C14–C12–C13). Pf=182–183° C.
Microanalysis:theoretical: % C(60.28); % H (7.84); % N (5.45); % S (12.44); analysis % C (60.497); % H (7.724); % N (5.322); % S (12.542).

B) morpholine-4-tetrahydro-4,5,6,7-benzothiophene (IC180)

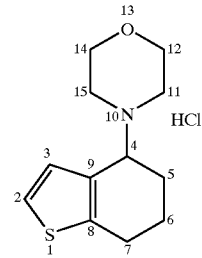

The raw amine was recrystallized in ether. Yield is quantitative.
Base
NMR $^1H$ (CDCl3) δ ppm: 7.05 (t, 2H, H2–H3); 3.71 (m, 5H, H4–H12–H14); 2.74–2.55 (m; 5H; H7–H11–H15); 1.74 (m, 4H, H5–H6).

NMR $^{13}C$ (CDCl3) δ ppm: 137.2 (C9); 136.8 (C8); 127 (C3); 121.3 (C2); 67.9 (C12–C14); 60.7 (C4); 49.03 (C11–C15); 25.51 (C7); 22.75 (C5); 22.06 (C6).

Hydrochloride:
NMR ¹H (CDCl3) δ ppm: 11.8 (s, 1H, ammonium); 7.57–7.54 (2d, 2H, H2–H3) J23=0.69; 4.7 (t, 2H, H12); 4.4 (t, 1H, H4); 3.95 (t, 2H, H14); 3.38–3.04–2.85 (m, 6H, H7–H11–H15); 2.24–1.98 (m, 4H, H5–H6).
NMR ¹³C (CDCl3) δ ppm: 142.2 (C9); 128.1 (C3); 126.58 (C8); 124.06 (C2); 63.43–62.6 (C12–C14); 61.25 (C4); 49.58 (C11); 46.25 (C15); 25 (C7); 23.4 (C5); 22.5 (C6). Pf=197–197.3° C.
microanalysis: theoretical % C(55.533); % H (6.935); % N (5.394); % O (6.165); % S (12.33); analysis % C (55.461); % H (6.927); % N (5.42); % O (6.289); % S (12.315).

C) thiomorpholine-4-tetrahydro-4,5,6,7-benzothiophene (IC193)

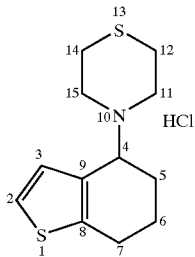

The reaction of reductive amination was effected with 0.7 eq of NaBH₃CN. The amine was chromatographed on neutral alumina; eluent petroleum ether/ether (60/40). Yield=63%

Base:
NMR ¹H (CDCl3) δ ppm: 7.04 (s, 2H, H2–H3); 3.79 (t, 1H, H4); 2.81–2.64 (m, 10H, H11–H12–H14–H15–H17); 2.2–1.59 (m, 4H, H5–H6).
NMR ¹³C (CDCl3) δ ppm: 138.6 (C9); 138 (C8); 126 (C3); 122 (C2); 62 (C4); 50.6 (C11–C15); 28.66 (C12–C14); 25 (C7); 23.3 (C5); 22 (C6).
Hydrochloride:
NMR ¹H (CDCl3) δ ppm: 7.59–7.57 (2d, 2H, H2–H3) J23=0.85; 4.22 (t, 1H, H4); 4.69–3.68–3.27–3–2.8–2.56 (m, 10H, H7–H11–H12–H14–H15); 2.16–1.87 (m, 4H, H5–H6).
NMR ¹³C (CDCl3) δ ppm: 142.71 (C9); 127.72 (C3); 127.01 (C8); 124.01 (C2); 62.80 (C4); 53 (C11–C15); 48.6 (C12–C14); 24.82 (C7); 24.49 (C5); 22.18 (C6). Pf=201.7–201.9° C.
microanalysis: theoretical % C(52.298); % H (6.532); % N (5.08); % S (23.224); analysis % C (52.476); % H (6.686); % N (5.06); % S (23.49).

D) N-methyl-piperazine-4-tetrahydro-4,5,6,7-benzothiophene (IC194)

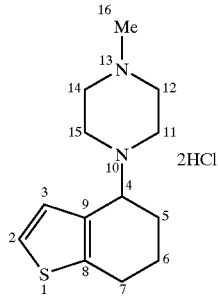

The reaction of reductive amination was effected with 0.7 eq of NaBH₃CN. The amine was chromatographed on neutral alumina; eluent petroleum ether/ether (60/40). Yield=50%.

Base:
NMR ¹H (CDCl3) δ ppm : 7.03–7.02 (d, 2H, H2–H3); 3.79 (t, 1H, H4); 2.28 (s, 3H, Me); 2.75–0.89 (m, 14H, CH2).
NMR ¹³C (CDCl3) δ ppm: 137.77 (C9); 137.46 (C8); 127.26 (C3); 121.22 (C2); 60.79 (C4); 55.68 (C12–C14); 45.91 (C16–C11–C15); 24.93 (C7); 22.54 (C5); 21.34 (C6).
Hydrochloride:
NMR ¹H (CDCl3) δ ppm: 7.525–7.38 (2d, 2H, H2–H3) J23=057; 4.81 (t, 1H, 1H4); 2.92 (s, 3H, Me); 4.5 to 1.54 (m, 14H, CH2).
NMR ¹³C (CDCl3) δ ppm: 143.77 (C9); 127.07 (C8); 126.01 (C3); 124.67 (C2); 61.73 (C4); 49.72–49.44 (C12–C14); 46.23 (C16); 42.75–42.38 (C11–C15); 24.27 (C7); 21.94 (C5); 21.64 (C6). Pf=176° C.
microanalysis: theoretical % C(50.522); % H (7.12); % N (9.06); % S (10.355); analysis % C (50.6); % H (7.37); % N (8.75); % S(10.38).

E) (4 hydroxy-piperidine)-4-tetrahydro-4,5,6,7-benzothiophene (IC209)

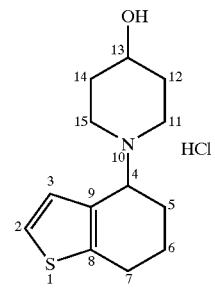

The reaction of reductive amination was effected with 0.7 eq of NaBH₃CN. The amine was chromatographed on neutral alumina; eluent petroleum ether/ether (80/20). Yield=47%.

Base:
NMR ¹H (CDCl3) δ ppm: 7.05 (t, 2H; H2–H3); 3.8 (t, 1H, H4); 3.69 (m, 1H, H13); 2.73 to 1.4 (m, 14H, CH2).
NMR ¹³C (CDCl3) δ ppm: 137.95 (C9); 137.5 (C8); 127.15 (C3); 121.3 (C2); 61.14 (C4); 44.65 (C11–C15); 35.28–35.1 (C12–C14); 24.96 (C7); 22.73 (C5); 21.35 (C6).
Hydrochloride:
NMR ¹H (DMSO) δ ppm: 10.86 (s, 1H, ammonium); 7.43–7.40 (2d, 2H, H2–H3) J23=0.83; 4.65 to 1.81 (m, 16H, alkyls).
NMR ¹³C (DMSO) δ ppm: 142.2 (C9); 128.9 (C8); 127.81 (C3); 123.7 (C2); 64.83 (C13); 59.9 (C4); 49.2–45.12 (C11–C15); 30.9–29.3 (C12–C14); 24.16 (C7); 21.72 (C5); 21.4 (C6). Pf=220–220.7° C.
microanalysis: theoretical % C(57.058); % H (7.31); % N (5.117); % O (5.846); analysis % C (57.25); % H (7.485) % N (5.362); % O (6.23).

F) amino-4-tetrahydro-4,5,6,7-benzothiophene (IC088 or IC140)

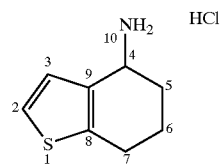

The reaction of reductive amination was effected with 0.7 eq of NaBH₃CN, at room temperature for 1 week. The amine was chromatographed on neutral alumina; eluent CH2Cl2+1% MeOH. Yield=88%.
Base:
NMR ¹H (CDCl3) δ ppm: 7.05 (t, 2H, H2–H3); 3.95 (t, 1H, H4); 2.77 (t, 2H, NH2); 2.2–1.42 (m, 6H, CH2).
NMR ¹³C (CDCl3) δ ppm: 139.2 (C9); 136.5 (C8); 128.36 (C3); 122.18 (C2); 47.39 (C4); 33.63 (C7); 24.97 (C5); 20.94 (C6).
Hydrochloride:
NMR ¹H (CDCL3+1% DMSO) δ ppm: 8.66 (s, 3H, ammonium); 7.2–7.18 (2d, 2H, H2–H3) J23=0.39; 4.32 (t, 1H, H4); 2.71 to 1.67 (m, 6H, cH2).
NMR ¹³C (CDCL3+1% DMSO) δ ppm: 140.68 (C9); 130.69 (C8); 124.13 (C3); 123.45 (C2); 46.55 (C4); 28.27 (C7); 24.82 (C5); 20 (C6). Pf=224.5–225.3° C.
microanalysis: theoretical % C(50.69); % H (6.331); % N (7.386); % S (16.88); analysis % C (50.94); % H (6.438); % N (7.507); % S (16.514).

G) amino-7-tetrahydro-4,5,6,7-benzothiophene (IC178)

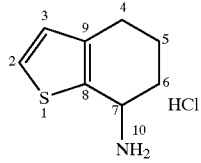

The reaction of reductive amination was effected with 0.7 eq of NaBH3CN. The amine was chromatographed on neutral alumina; eluent CH2Cl2+1% MeOH. Yield=42%.
Base:
NMR ¹H (CDCL3) δ ppm: 6.94 (2d, 2H, H2–H3) J23=0.38 ppm; 4.08 (t, 1H, H7); 2.6 (m, 2H, NH2); 2.21 to 1.45 (m, 6H, H4–H5–H6).
NMR ¹³C (CDCL3) δ ppm: 141.65 (C9); 136.1 (C8); 127.36 (C3); 123.03 (C2); 48.27 (C7); 35.5 (C4); 25.5 (C6); 21.4 (C5).
GC-MS: 60° C./10° min/250° C.; 12.03 min; 153/125/110/97180.
Hydrochloride:
NMR ¹H (CDCL3+1% DMSO) δ ppm: 8.79 (s, 3H, ammonium); 6.96–6.88 (2d, 2H, H2–H3) J23=0.45; 4.43 (t, 1H, H7); 2.642 to 1.78 (m, 6H, CH2).
NMR ¹³C (CDCL3+1% DMSO) δ ppm: 139.67 (C8); 132.13 (C9); 128.52 (C3); 125.44 (C2); 46.55 (C7); 29.5 (C4); 26.42 (C6); 20 (C5). Pf=205–205.5° C.
microanalysis: theoretical % C(50.693); % H (6.331); % N (7.386); % S (16.883); analysis % C (50.83); % H (6.256); % N (7.205); % S (17.037).

H) piperidino-7-tetrahydro-4,5,6,7-benzothiophene (IC146)

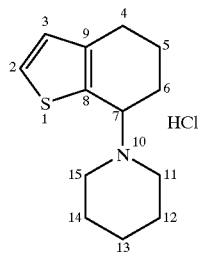

The amine was chromatographed on neutral alumina; eluent petroleum ether/ether (50/50).
Base:
NMR ¹H (CDCL3) δ ppm: 6.95–6.93 (2d, 2H, H2–H3); 3.99 (t, 1H.H7); 3.05 to 1.45 (m, 16H, CH2).

NMR ¹³C (CDCL3) δ ppm: 140 (C9); 137.45 (C8); 127.21 (C3); 123.92 (C2); 62.26 (C7); 51.05–49.71 (C11–C15); 26.53–25.57–24.83–22.71–22.66–22.03 (C4–C5–C6–C12–C13–C14).
Hydrochloride:
NMR ¹H (CDCL3) δ ppm: 11.79 (s, 1H, ammonium); 7.09–7.06 (2d, 2H, H2–H3) J23=0.48; 4.62 (t, 1H, H7); 3.42 to 1.33 (m, 16H, cH2).
NMR ¹³C (CDCL3) δ ppm: 143.31 (C9); 127.94 (C3); 126.87 (C2); 125.41 (C8); 62.16 (C7); 51.806–48.96 (C11–C15); 25.38–22.96–22.43–22.24–20.93 (C4–C5–C6–C12–C13–C14). Pf=171–172° C.
microanalysis: theoretical % C(60.68); % H (7.84); % N (5.45); % S (12.44); analysis % C (60.75); % H (7.79); % N (5.365); % S (12.21).

I) morpholino-4-tetrahydro-4,5,6,7-benzothiophene (IC2–16)

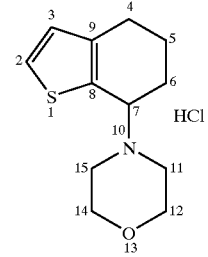

The amine was chromatographed on neutral alumina; eluent petroleum ether/ether (60/40). Yield=58%.
Base
NMR ¹H (CDCl3) δ ppm: 7.15–6.74 (2d, 2H, H2–H3) J23=0.4; 3.71 (m, 5H, H7–H12–H14); 2.70–2.55 (m; 5H; H4–H11–H15); 1.98–1.70 (m, 4H, H5–H6).
NMR ¹³C (CDCl3) δ ppm: 138.62 (C9); 137.64 (C8); 127.34 (C3); 123.88 (C2); 67.52 (C12–C14); 61.63 (C7); 48.77 (C11–C15); 25.51 (C4); 22.44 (C5); 22.08 (C6).
Hydrochloride:
NMR ¹H (CDCl3) δ ppm: 7.31–6.82 (2d, 2H, H2–H3) J23=0.49; 4.64–1.19 (m, 14H, H7–H12–H14–H4–H11–H15–H5–H6).
NMR ¹³C (CDCl3) δ ppm: 143.58 (C9); 128.05 (C3); 127.31 (C2); 124.56 (C8); 63.68–63.26 (C12–C14); 62.17 (C7); 48.33 (C11–C15); 25.26 (C4); 24.99 (C5); 20.52 (C6). Pf=172.6–172.7° C.
microanalysis: theoretical % C(55.53); % H (6.93); % N (5.39); % S (12.33); analysis % C (55.54); % H (6.80); % N (5.55); % S (12.43).

J) piperidino-4-tetrahydro-4,5,6,7-thio-7-benzothiophene (IC237)

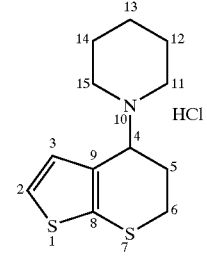

The amine was chromatographed on neutral alumina; eluent petroleum ether. Yield=70%.
Base:
NMR ¹H (CDCl3) δ ppm: 7.09–6.98 (2d, 2H, H2–H3) J23=0.104; 3.78 (t, 1H, H4); 3.14–0.93 (m, 14H, CH2).

NMR $^{13}$C (CDCL3) δ ppm: 134.68 (C9); 129.93 (C8); 128.58 (C3); 119.83 (C2); 60.32 (C4); 49.99 (C11–C15); 27.31 (C6–C5); 22.50 (C12–C14–C13).
Hydrochloride:
NMR $^1$H (CDCL3) δ ppm: 11.93 (s.1H, ammonium); 7.49–7.46 (2d, 2H, H2–H3) J23=0.602; 4.78 (t, 1H, H4); 3.52 to 1.32 (m, 14H, CH2).
NMR $^{13}$C (CDCL3) δ ppm: 136.9 (C9); 129 (C3); 124.12 (C8); 122.73 (C2); 60.07 (C4); 51.47–49.45 (C11–C15); 26.91 (C6); 24.42 (C5); 22.89–22.41 (C12–C14); 22.24 (C13). Pf=177.9–187.1° C.
microanalysis: theoretical % C(52.298); % H (6.532); % N (5.08); % S (23.22); analysis % C (52.281); % H (6.583); % N (4.871); % S (23.481).
K) morpholine-4 tetrahydro-4,5,6,7-thio-7-benzothiophene (IC241)

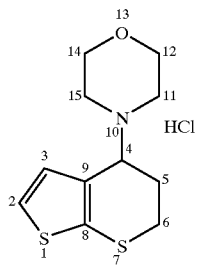

The amine was recrystallized in ether. Yield=65%.
Base:
NMR $^1$H (CDCL3) δ ppm: 7.02–7 (2d, 2H, H2–H3) J23=0.05 ppm; 3.7 (m, 5H, H4, H12, H14); 3.2 to 2.1 (m, 8H, H5–H6–H11–H15).
NMR $^{13}$C (CDCL3) δ ppm: 130.33 (C9); 126.98 (C3); 122 (C8); 118.14 (C2); 67.45 (C12–C14); 60.75 (C4); 52–49.4 (C1–C15); 26.47 (C5); 22.8 (C6).
Hydrochloride:
NMR $^1$H (DMSO) δ ppm: 11.12 (s, 1H, ammonium); 7.47 (d, 2H, H2–H3) J23–0.06; 4.72 (t, 1H, H3); 3.94 to 2.12 (m, 12H, CH2).
NMR $^{13}$C (DMSO) δ ppm: 136.9 (C9); 130.07 (C3); 123.98 (C8); 122.12 (C2); 63.28–62.99 (C12–C14); 59.07 (C4); 50.27–47.83 (C11–C15); 23.92 (CS); 22.22 (C6). Pf=192.8–192.9° C.
microanalysis: theoretical % C(47.59); % H (5.76); % N (5.04); analysis % C (47.498); % H (6.088); % N (4.886).
L) (N-methyl piperazine)-4-tetrahydro-4,5,6,7-thio-7-benzothiophene (IC242)

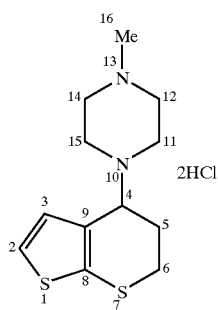

The amine was chromatographed on neutral alumina; eluent petroleum ether/ether (60/40). Yield=77%.
Base:
NMR $^1$H (CDCL3) δ ppm: 7.17–7.14 (2d, 2H, H2–H3); 3.8 (t, 1H, H4), 3.44–2.09 (m, 13H, H14–H5–H6–H11–H12–H14–H15), 2.18 (s, 3H, H16).

Hydrochloride:
NMR $^1$H (DMSO) δ ppm: 12.02 (s, 1H.ammonium), 7.49 (d, 2H, H2–H3), 4.75 (s, 1H, ammonium), 3.64–2.13 (m, 13H, H4–H5–H6–H11–H12–H14–H15), 2.84 (s, 3H, H16).
NMR $^{13}$C (DMSO) δ ppm: 136.04 (C9), 129.5 (C3), 124.74 (68), 122.25 (C2), 58.87 (C4), 49.93 (C12–C14), 46.73 (616), 42.17 (C11), 41.01 (C15), 24.88 (C6), 22.81 (C5). Pf=156.8–157.5° C.
microanalysis: theoretical % C(44.069); % H (6.115); % N (8.56); % S (19.57) analysis % C (44.185); % H (6.242); % N (8.69); % S (19.796).
M) piperidino-1-tetrahydro-1,2,3,4-thio-9-fluorene (IC207)

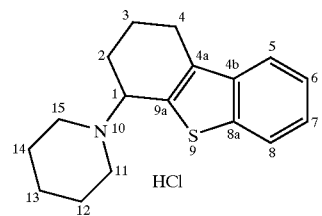

The reaction of reductive amination was effected with 0.7 eq of NaBH$_3$CN and 1 eq of pyridine. The amine was chromatographed on neutral alumina; eluent petroleum ether/ether (80/20). Yield=30%.
Base:
NMR $^1$H (CDCL3) δ ppm: 8.5–7.78 (2d, 2H, H5–H8); 7.27 (m, 2H, H6–H7); 4.15 (t, 1H, H1); 2.84 to 1.43 (m, 16H, CH2).
NMR $^{13}$C (CDCL3) δ ppm: 140 (C8a); 139.35 (C9a); 138.06 (C4b); 130.64 (C4a); 124.25–123.35–123.25–121.6 (C5, C6, C7, C8); 60.86 (C1); 49.35 (C11–C15); 26.66–26.19–25–22.36–21.22(C2–C3–C4–C12–C13–C14).
Hydrochloride:
NMR $^1$H (CDCL3) δ ppm: 11.58 (s.1H, ammonium); 7.83–7.45 (2d, 2H, H5–H8); 7.39 (m, 2H, H6–H7); 4.53 (s, 1H, H1); 3.8 to 1.3 (m, 16H, CH2).
NMR $^{13}$C (CDCL3) δ ppm: 147.47 (C8a); 138.57 (4b); 138.28 (C9a); 124.76–124.26–122.65–120.77 (C5–C6–C7–C8); 122 (C4a); 60.35 (C1); 53.65 (C15); 52.8 (C11); 24.64–24.59–22.84–22.38–21.83–17.2 (C2–C3–C4–C12–C13–C14). Pf=201.7–202° C.
microanalysis: theoretical % C(66.37); % H (7.15); % N (4.551); analysis % C (66.59); % H (7.33); % N (4.251)
N) morpholine-1-tetrahydro-1,2,3,4-thio-9-fluorene (IC219)

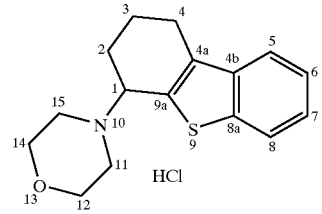

The reaction of reductive amination was effected with 0.7 eq of NaBH$_3$CN and 1 eq of pyridine. The amine was chromatographed on neutral alumina; eluent petroleum ether/ether (80/20). Yield=30%
Hydrochloride:
NMR $^1$H (CDCL3) δ ppm: 11.9 (s, 1H, ammonium); 7.78 (d, 2H, H aromatic); 7.32 (m, 2H, H aromatic); 4.86 (m, 1H, H1); 4.5 to 1.24 (m, 14H, CH2).
NMR $^{13}$C (CDCL3) δ ppm: 169.52 (C8a); 148.1 (C4b); 138.37 (C9a); 124.86–124.38–122.75 (C5–C6–C7–C8;

120.57 (C4a); 63.42–63.21 (C12–C14); 60.96 (C1); 51.63 (C11–C15); 24.63–24 (C2–C4); 17.59 (C3). Pf=198.4–198.5° C.
microanalysis: theoretical % C(62.06); % H (6.459); % N (4.522); analysis % C (62.084); % H (6.445); % N (4.92).
O) N-methyl-piperazine-1-tetrahydro-1,2,3,4-thio-9-fluorene (IC2–38)

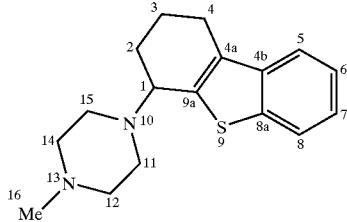

Base:
NMR $^1$H (CDCL3) δ ppm: 8.34 (d, 1H, H8); 7.72 (d, 1H, H5); 7.28 (m, 2H, H6–H7); 4.1 (t, 1H, H1), 2.28 (s, 3H, Me), 2.83–1.7 (m, 14H, CH2).
NMR $^{13}$C (CDCL3) δ ppm: 140.32 (C8a); 139.98 (C9a); 138.41 (C4b); 130 (C4a); 124.12–123.62–123.54–121.89 (C5–C6–C7–C8); 59.86 (C1); 55.90 (C12–C14–C11–C15); 46.29 (C16); 26.17–22.99–21.65 (C2–C3–C4). Pf=205.2–205.3° C.
microanalysis: ($C_{17}H_{22}SN_2$.2HCl.$H_2O$) theoretical % C(54.14); % H (6.89); % N (7.42); analysis % C (54.18); % H (6.5); % N (7.47).
P) thio-1-piperidino-4 tetrahydro-1,2,3,4-thio-9-fluorene (IC249)

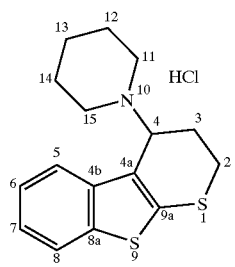

The medium was held under reflux for 8 days. The amine was chromatographed on neutral alumina; eluent petroleum ether/ether (60/40). Yield=57%. (In the same conditions with addition of 1 eq of LiCl during the reaction of reductive amination. Yield=80%).
Base:
NMR $^1$H (CDCL3) δ ppm: 8.08 (d, 1H, H5), 7.68 (d, 1H, H8), 7.28 (m, 2H, H6–H7), 4.06 (t, 1H, H4), 3.13–0.89 (m, 14H, CH2).
Hydrochloride:
NMR $^1$H (DMSO) δ ppm: 10.22 (s, 1H, ammonium), 8.02 (d, 1H, H5), 7.95 (d, 1H, H8), 7.39 (m, 2H, H6–H7), 5.05 (t, 1H, H4), 4.50–1.36 (m, 14H, CH2).
NMR $^{13}$C (DMSO) δ ppm: 140.53 (C8a), 139.79 (C4b), 136.05 (C4a), 125.15 (C9a), 123.88–122.28–120.76–118.45 (C5–C6–C7–C8) 56.97 (C4), 52.14–51.07 (C11–C15), 22.55 (C2), 22.24 (C12–C14–C3), 21.45 (C13). Pf=169.2–169.4° C.
microanalysis: theoretical % C(59.01); % H (6.14); % N (4.23) analysis % C (59.09); % H (6.29); % N (4.11).

Q) thio-1-morpholino-4-tetrahydro-1,2,3,4-thio-9-fluorene (IC2–19)

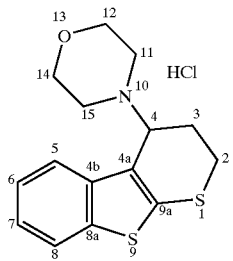

The amine was recrystallized in ether. Yield=60%
Base:
NMR $^1$H (CDCL3) δ ppm: 7.91 (d, 1H, H5), 7.68 (d, 1H, H8), 7.33 (m, 2H, H6–H17), 4.02 (t, 1H, H4), 3.70–0.90 (m, 12H, CH2).
NMR $^{13}$C (CDCL3) δ ppm: 140.09 (C8a), 137.1 (C4b), 134.81 (C4a), 124.99 (C9a), 123.9–123.07–121.39–121.35 (C5–C6–C7–C8), 67.47 (C12–C14), 56.56 (C4), 49.89 (C11–C15), 25.16 (C2), 23.91 (C3).
Hydrochloride:
NMR $^1$H (CDCL3) δ ppm: 12.08 (s, 1H, ammonium), 7.72 (m, 2H, H5–H8), 7.33 (m, 2H, H6–H7), 4.93 (t, 1H, H4), 4.51–2.92 (m, 12H, CH2).
NMR $^{13}$C (CDCL3) δ ppm: 142.7 (C8a), 138.66 (C4b), 136.97 (C4a), 125.26 (C9a), 124.13–122.22–119.19–116.01 (C5–C6–C7–C8), 63.58–63.12 (C12–C14), 59.44 (C4), 53.25–50.72 (C11–C15), 30.85 (C2), 23.85 (C3). Pf=128.6–128.7° C.
microanalysis: (C15H17NOS2.HCl).½($H_2O$) theoretical % C(53.52); % H (5.35); % N (4.16); % S (19.01); % O (7.13) analysis % C (53.20); % H (5.77); % N (4.3); % S (19.00); % O (7.30).
R) thio-1-(N-methyl piperazine)-4-tetrahydro-1,2,3,4-thio-9-fluorene (IC2–21)

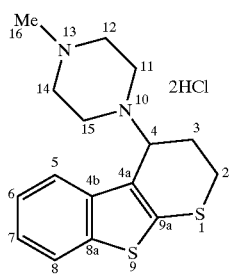

The amine was chromatographed on neutral alumina; eluent petroleum ether/ether (60/40). Yield=68%.
Base:
NMR $^1$H (CDCL3) δ ppm: 7.92 (d, 1H, H5), 7.66 (d, 1H, H8), 7.24 (m, 2H, H6–H7), 4.04 (t, 1H, H4), 3.33–0.85 (m, 12H, CH2), 2.26 (s, 3H, Me).
NMR $^{13}$C (CDCL3) δ ppm: 140.16 (C8a), 137.05 (C4b), 134.39 (C4a), 125.58 (C9a), 123.81–123–121.72–121.28 (C5–C6–C7–C8), 56.42 (C4), 55.64 (C12–C14), 49.1 (C16), 45.95 (C11–C15), 25.50 (C2), 23.95 (C3).
Hydrochloride:
NMR $^1$H (DMSO) δ ppm: 11.71 (s, 1H, ammonium), 7.94 (d, 2H, H5–H8), 7.39 (m, 2H, H6–H7), 4.89 (s, 1H, ammonium), 3.51–1.90 (m, 13H, CH2–H4), 2.79 (s, 3H, Me).
NMR $^{13}$C (DMSO) δ ppm: 139.60 (C8a), 136.21 (C4b–C4a), 125.06 (C9a), 123.86–122.22–120.90

(C5–C6–C7–C8), 56.57 (C4–C12–C14), 47.55 (C16), 47.55–46.28 (C11–C15), 22.7 (C2), 22.58 (C3). Pf=165–165.2° C.

microanalysis: theoretical % C(50.96); % H (5.83); % N (8.49); % S (16.97) analysis % C (50.49); % H (5.93); % N (8.36); % S (16.99).

β) investigation of the biological properties of the compounds of the invention

A) Chemical test of capture of OH• radicals:

(Free Rad. Res. Comms., Vol. 14, Nos. 5–6, pp. 363–372) Reaction:

200 ml of buffer (30 mM $Na_2HPO_4.7H_2O$, 40 mM NaCl, 0.1 mM EDTA), 125 ml of deoxyribose at $2.10^{-3}$ mM and 125 ml of 4-times concentrated solution of radical inhibitor (final concentration from 0 to 0.5 mM) were placed in glass haemolysis tubes cooled on an ice bath. 50 ml of $FeSO_4$ at $10^{-3}$ mM (in water) is added at time 0. After 15 min of incubation the reaction is stopped with 250 ml of trichloroacetic acid at 3%, to which is added 250 ml of solution of thiobarbituric acid at 1.5% (in water). The tubes are kept at 100° C. for 10 min then cooled for detection with UV at 532 nm. The linear relation A0/A=1+ks/dkr [(competitor)/(2-deoxyribose)] was used, where A0 and A denote the absorbances in the absence and in the presence of competitor, ks is the rate constant of reaction of the competitor with OH• and kdr=$1.9*10^9$ $M^{-1}$ $sec^{-1}$ is the rate constant of reaction of 2-deoxyribose with OH•. Thus ks is equal to the gradient of the straight line A0/A f((competitor)/(2-deoxyribose)) multiplied by kdr.

Chemical test of capture of OH• radicals (p 36 of the preceding document)

| Compound | $k_s$ ($10^{-9}M^{-1}$ $sec^{-1}$) (±SEM) |
|---|---|
| D-mannose | 0.94 ± 0.06 |
| vitamin C | 1.87 ± 0.17 |
| TCP | 2.75 ± 0.13 |
| ac.salicyl. | 3.02 ± 0.18 |
| IC088 | 3.37 ± 0.25 |
| IC023 | 3.61 ± 0.16 |
| IC193 | 3.41 ± 0.25 |
| IC180 | 3.75 ± 0.33 |
| IC194 | 3.50 ± 0.23 |
| IC209 | 3.27 ± 0.50 |
| IC178 | 2.76 ± 0.06 |
| IC163 | 2.80 ± 0.26 |
| IC2-16 | 3.33 ± 0.15 |
| IC237 | 3.45 ± 0.19 |
| IC241 | 3.01 ± 0.14 |
| IC242 | 3.00 ± 0.19 |

The derivatives of the invention are all, chemically, scavengers of OH•. They are for the most part more effective for some (5 compounds between 3.37 and 3.75) than salicylic acid (3.02±0.18) and far better than vitamin C (1.87±0.17) or D-mannose (0.94±0.06).

B) Procedure with cultures of astrocytes and generation of radicals by the xanthine/xanthine oxidase (X/XO) pair Culture:

400 µl of D-lysine at 25 µg/ml (9 ml of D-lysine at 100 µg per ml of borate buffer (0.1M pH 8.4)+27 ml of water) is placed in each well of 24-well culture plates. The wells are left in the stove (5% $CO_2$, 37° C.) over night. Each well is rinsed with 2 times 750 µl of Hanks before receiving the culture medium. 3 lateral demi cortices are taken from rats aged 1 to 2 days. (The hippocampus, the striatum and the meninges are removed). The demi cortices are placed in 2 ml of trypsin-EDTA then put in the stove for 30 min. The action of the trypsin is stopped with 10% of decomplemented foetal calf serum (200 µl). The serum and the trypsin are removed then the cells are dissociated with a pipette in 10 ml of medium (MEM 225 ml+FCS-D 25 ml+glucose 20% 7.5 ml) (MEM=minimum essential medium; FCS-D= decomplemented foetal calf serum). The culture medium is made up to 30 ml, stirred and placed at 400 µl per well. The medium is changed twice weekly for 18 days. The last replacement is effected 4 days prior to the treatment, with a medium without decomplemented foetal calf serum. (MEM 31.5 ml+glucose 20% 1.05 ml).

Treatment takes place on the 18th or 19th day.

Product testing:

Each well is washed with 750 µl of buffer (NaCl 124 mM, KCl 4.6 mM, $CaCl_2$ 1.2 mM, $MgCl_2$ 1.3 mM, $KH_2PO_4$ 0.416 mM, $NaHCO_3$ 26.75 mM, glucose 10 mM; pH 7.4) for 10 min. The cells are incubated in the presence of xanthine (500 µM) and of the test product (from 0 to 1 mM). After 10 min, xanthine oxidase is added (50 mU/ml) and it is again left to incubate for 10 min. Release of radicals is stopped by washing 3 times with catalase (3000 U/ml). The glutamate is then recaptured in a solution of radioactive glutamate ($^3H$) at 40 µM (isotopic dilution 1/20000). Recapture is stopped by washing 3 times with the cold buffer. The cells are detached with soda 0.2N and the radioactivity is measured.

Controls

Firstly we checked that the inhibition of recapture observed in the presence of X/XO is indeed due to a radical process. For this we replaced the test products with two enzymes: SOD (SuperOxide Dismutase) and catalase (FIG. 1). Whereas SOD (which activates the dismutation of the superoxide anion radicals to hydrogen peroxide) cannot by itself counteract the effect of X/XO, catalase (which converts hydrogen peroxide to oxygen and water) allows a normal degree of recapture to be attained. The Fenton reaction converting hydrogen peroxide to OH• is thus short-circuited. This test does not completely differentiate the respective effects of $H_2O_2$ and OH•. However, as there seems to be sufficient reducing agent in the medium to promote the formation of $H_2O_2$ starting from $O_2.^-$, it appears likely that a substantial proportion of $H_2O_2$ gives OH• (a highly reactive radical).

Secondly, we turned our attention to the relation that exists between the quantity of radicals (here the quantity of X/XO) and the percentage inhibition. As can be seen from FIG. 2, this relation is linear (at least in the range of concentrations used). This result therefore enables us to predict the type of curve expected in the presence of product.

FIGS. 3 to 8 are the mean of at least 4 independent tests in which the protective power of IC180, IC023, IC241, IC2–16, IC178, IC140, IC209, IC237, IC146, IC193, IC194, IC242, IC207, IC2–19, IC219, IC2–21, and IC249, as a function of the dose, was tested against a fixed concentration of radicals, and therefore of X/XO. In the case of IC180, the increase in recapture appears to be linear (up to 100% is found in some tests). In addition we showed that the product alone (without the presence of X/XO) has no effect on recapture. As for IC023, the start of the curve is comparable but, starting from 15% recapture, the opposite effect is observed. Since IC023 alone only becomes "toxic" starting from 1 mM, the variation observed starting from 0.6 mM might reflect the existence of metabolites that are poorly tolerated by the cells. The derivative morpholine IC180 is more interesting.

Action of the derivatives on xanthine oxidase:
(Free Radical Biology & Medicine, Vol 20, No 1, pp.35–43, 1996)

As the tests were carried out in the presence of X/XO, we checked that these results were not due to inhibition of the enzyme.

5 ml of xanthine 20 mM in soda 0.1N and 100 mM and 500 mM of the test product in phosphate buffer at pH 7.4 were placed in a final volume of 2 ml. Reaction is started by adding 50 ml of solution of xanthine oxidase at 0.56 U/ml. Formation of urea is monitored by UV spectroscopy at 290 nm. Allopurinol is a reference inhibitor.

| Product | % inhibition 100 µM | % inhibition 500 µM |
|---|---|---|
| Allopurinol | 92% | 90% |
| IC180 | 0% | 2% |
| IC023 | −6% | — |
| IC194 | −15% | 10% |
| IC193 | −7% | −2% |
| IC237 | −9% | −8% |
| IC241 | 7% | −8% |
| IC140 | −15% | — |
| TCP | −10% | — |

The compounds of the invention are not by themselves inhibitors of XO.

C) tests in vivo on intracerebral perfusion and generation of radicals by injection of glutamate.

Experimental preparation: [J. Neurosci. Methods, 72 (1997) 123–135]

The animals used are male rats of the Wistar strain weighing 250 g. Under general anaesthesia, the animals are placed in a stereotaxic apparatus. A cannula guide is introduced by microsurgery into the striatum (coordinates A : +0.02 cm; L: −0.30 cm and H: −0.65 cm relative to the 0 point defined according to Paxinos and Watson). Three to four screws are arranged on the animal's skull and the whole is fixed with dental cement (Durelon). After a recovery period during which the animals become used to the tester, a CMA 12 microdialysis cannula is inserted in the guide in such a way that the cellophane membrane projects 2 mm into the brain tissue. All the perfusions are effected on animals that are awake. A physiological solution (NaCl: 140 mM; KCl: 5 mM; CaC$_2$: 3.9 mM), to which 250 µM of Na salicylate is added extemporaneously, is injected into the system at a constant flow rate of 1 µl.min$^{-1}$. The fluid leaving the cannula is not collected for the first two hours of perfusion. Then samples are collected by fraction every 20 minutes for 8 hours, and are immediately frozen at −30° C.

Method of measurement:

Salicylic acid present in the perfusion fluid reacts with the OH radicals released at the perfusion site, forming a compound, 2,3-dihydroxybenzoic acid (2,3-DBHA), which is specific to this reaction. This reaction product is quantified in each sample by high-performance liquid chromatography followed by Electrochemical Detection. The stationary phase is a graft silica C18. The mobile phase is a solution (KH$_2$PO$_4$: 30 mM; EDTA: 0.1 mM; triethylamine 2 µM; sodium octanesulphonate 1.1 µM) containing 12% of a methanol/acetonitrile mixture at 2/1 and equilibrated to pH 3.28 with citric acid. This mobile phase is maintained at 25° C. and injected at a flow rate of 1.3 µl.min$^{-1}$. The oxidation potential is fixed at 0.55 Volts.

Analysis:

Analysis was effected in three stages.

Perfusion 1: after two hours of perfusion in normal conditions, for establishing the basic release profile of free radicals, the perfusion fluid was replaced with a medium containing in addition 1.5 mM of Na glutamate, with all the other components remaining identical to the initial medium. After 1 hour of perfusion with this mixture, the normal medium is reintroduced and perfusion continues. FIG. 9 shows that the introduction of glutamate causes, in the subsequent fractions, a considerable increase in release of 2.3-dihydroxybenzoic acid. Taking into account individual variations, this secretion profile, shown here for one individual, is reproducible (sensitivity, porosity of microdialysis). At the end of this perfusion, the microdialysis cannulae are removed from the brains and the animals are returned to their usual living conditions.

Perfusion 2: a week after perfusion 1, the animals undergo a new perfusion session with a protocol that is slightly different from the first session. One of the products of the invention is added to the perfusion medium, at a concentration of 1 mM, and its presence is maintained for one hour prior to introduction of the glutamate, during introduction of the glutamate, then an hour after the stimulus. FIG. 9 shows that the release of free radicals induced by the glutamate, and visualized by the variation in concentration of 2,3-dihydroxybenzoic acid, was completely blocked by injection of a compound of the invention. This blocking was observed for all the individuals tested.

Perfusion 3: a week after the second perfusion, the animals are perfused again according to a protocol identical to the first perfusion. FIG. 9, still for the same individual, shows firstly that the system is fully functional, in the sense that despite multiple introductions and extractions of the microdialysis cannula, despite multiple perfusions, despite multiple stimulations with glutamate, and despite the in situ treatment with the derivative IC 180, an injection of glutamate in the striatum is still able to promote local release of free radicals. This effect was observed for all the animals.

This shows firstly that during the second perfusion, absence of a reponse to glutamate stimulation was indeed due to the presence of the compound of the invention, and not to a possible deterioration of the physiology of the central nervous system. This shows in addition that introduction of the drug (IC 180) in situ did not have a toxic side effect, in the conditions of the investigation.

γ) the compounds of the invention are concentrated in the brain

Experimental preparation: [Amer. J. Physiol., 267 (1994) R164–R170]

Under general anaesthesia, catheters made from tubes of flexible and inert polyethylene PE50 (Clay Adams) are placed in the right carotid artery of male rats of the Wistar strain weighing 250 g, and are slid under the skin to emerge at the nape at a site that is inaccessible to the animal. The injections are carried out 5 days later, to allow the animals optimum post-operative recovery. This arrangement permits easy and very quick systemic injections on the animal while it is conscious.

Method of measurement:

At the specified time after injection, the animals are killed by decapitation. The brains are removed in less than a minute without further fractionation. The meninges are quickly separated and the brains are rinsed in a large volume of physiological serum before being frozen at −30° C. The blood is collected on EDTA in tubes maintained at 0° C. After centrifugation, the plasma is separated and aliquots are preserved at −30° C.

After thawing, the brains are weighed and homogenized in the cold in 3 volumes of NaOH (0.1N), using an Ultra-Turrax pulverizer. An internal standard, at a suitable concentration, is added to each sample to allow for individual variations in extraction. The pulverizates are directly extracted three times with a total of 6 volumes of ethyl acetate, followed each time by centrifugation at high speed.

Apart from the stage of pulverizing, the plasmas are treated similarly.

The extracts are filtered through a 0.22 μm Millipore membrane and, after evaporation of the solvent under a nitrogen stream, the dry extracts are stored at −30° C.

The presence and the concentration of the compound IC 180 in the samples was demonstrated by comparison with standard samples of known concentration after separation by high-performance liquid chromatography on a column of silica followed by UV detection at 230 nm.

Analysis:

One of the compounds of the invention (IC 180), diluted in physiological serum, is injected at a concentration equal to 20 mg.kg$^{-1}$. FIG. 10 shows that 30 min later, it is detected preferentially in the brain of the animals, and is clearly identifiable in the plasma. Its concentration decreases by about 50% in the brain, 1 hour after injection. However, in the plasma of the same animals, the drug can only be detected very slightly. The ratio of the concentrations between the brain and the plasma therefore increases between 30 and 60 minutes after injection.

Accordingly, it is shown that the drug:
  does not have a rapid toxic effect in the conditions of the investigation;
  penetrates readily and quickly to the central nervous system, where it is able to achieve its objectives.

Figure 1:
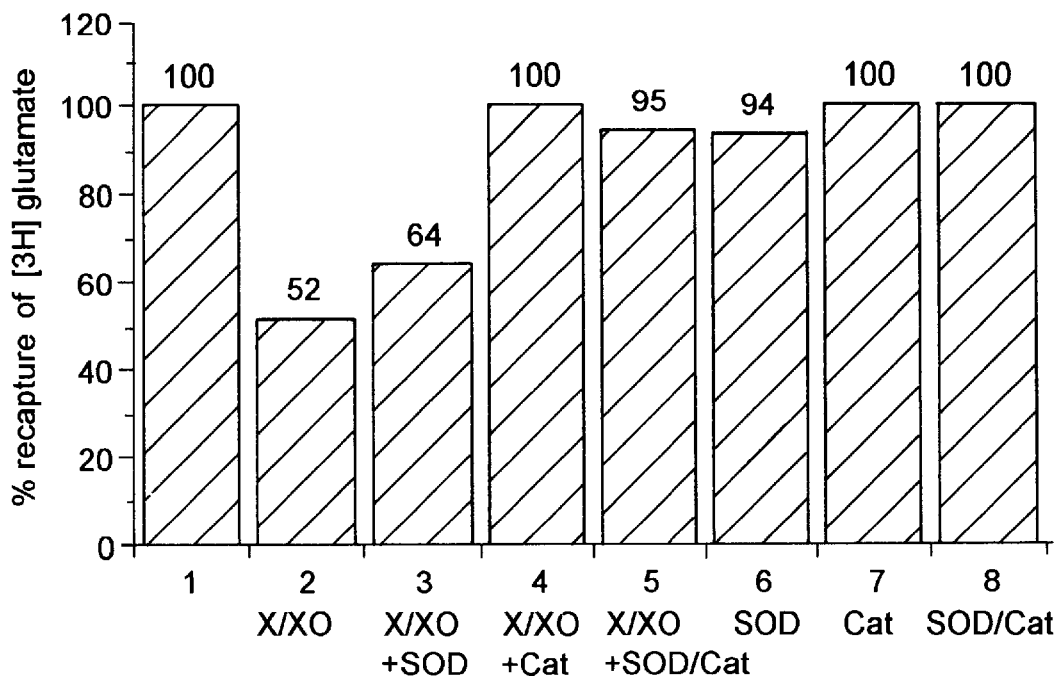
FIG. 1: bar chart of inhibition of recapture of glutamate by the astrocytes; the percentage recapture of [$^3$H]glutamate is shown on the ordinate; columns 1 to 8 correspond respectively to the percentages of recapture in the absence of X/XO (1), in the presence of X/XO (2), in the presence of X/XO and of SOD (3), in the presence of X/XO and of catalase (Cat) (4), in the presence of X/XO, SOD and of Cat (5), in the presence of SOD (6), in the presence of Cat (7), in the presence of SOD and of Cat (8).
Figure 2:
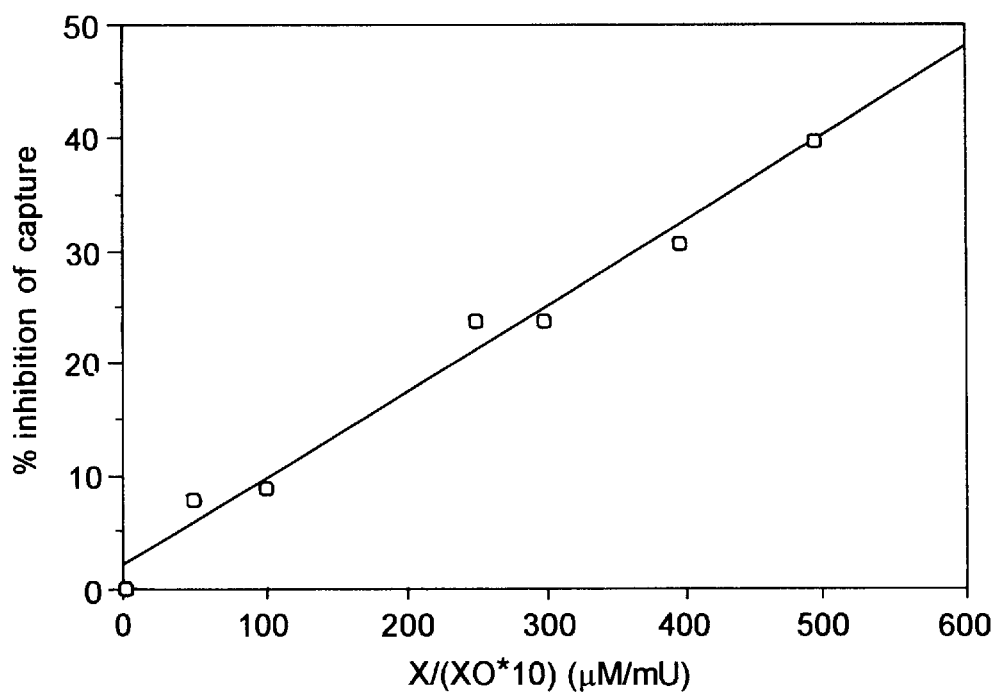
FIG. 2: curve of inhibition of recapture of glutamate by the astrocytes as a function of the concentration of X/XO; the percentage inhibition of recapture is shown on the ordinate; the concentrations of X/XO are shown on the abscissa in μM/mU (multiplied by 10 for XO (XO×10; mU=milliUnits).
Figure 3:
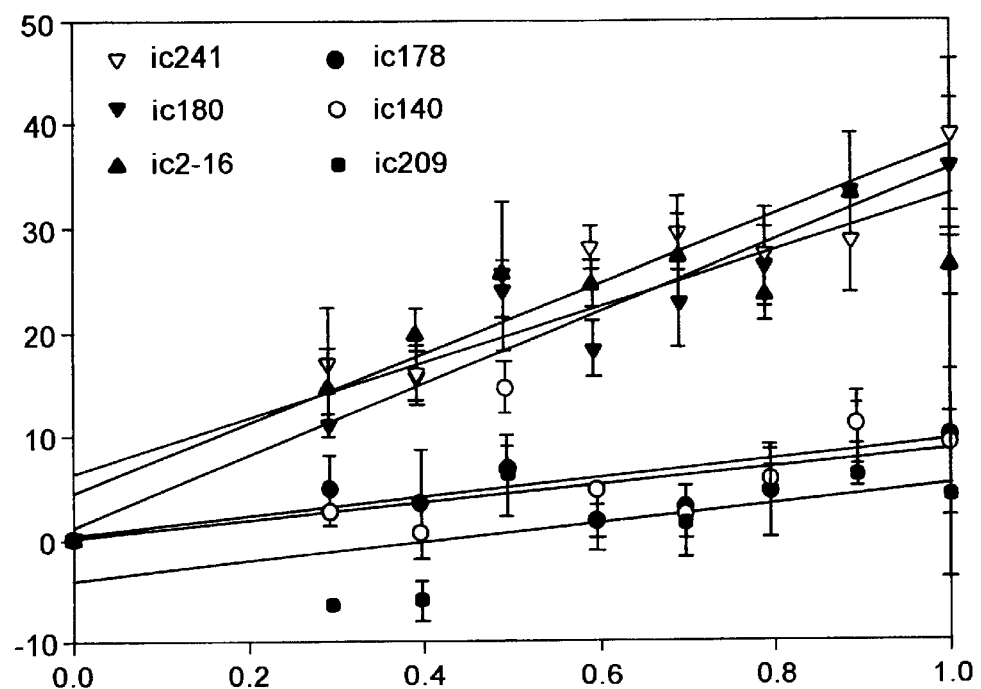
FIG. 3: curve of the recapture of glutamate by the astrocytes as a function of the concentration of compounds IC241 (▽), IC180 (▼), IC2–16 (▲), IC 178 (•), IC 140 (o), IC209 (■) and in the presence of a fixed quantity of X/XO producing 50% blocking of glutamate recapture; the percentage of recapture of [$^3$H]glutamate is shown on the ordinate, and the concentration (in mM) of the compounds is shown on the abscissa.
Figure 4:
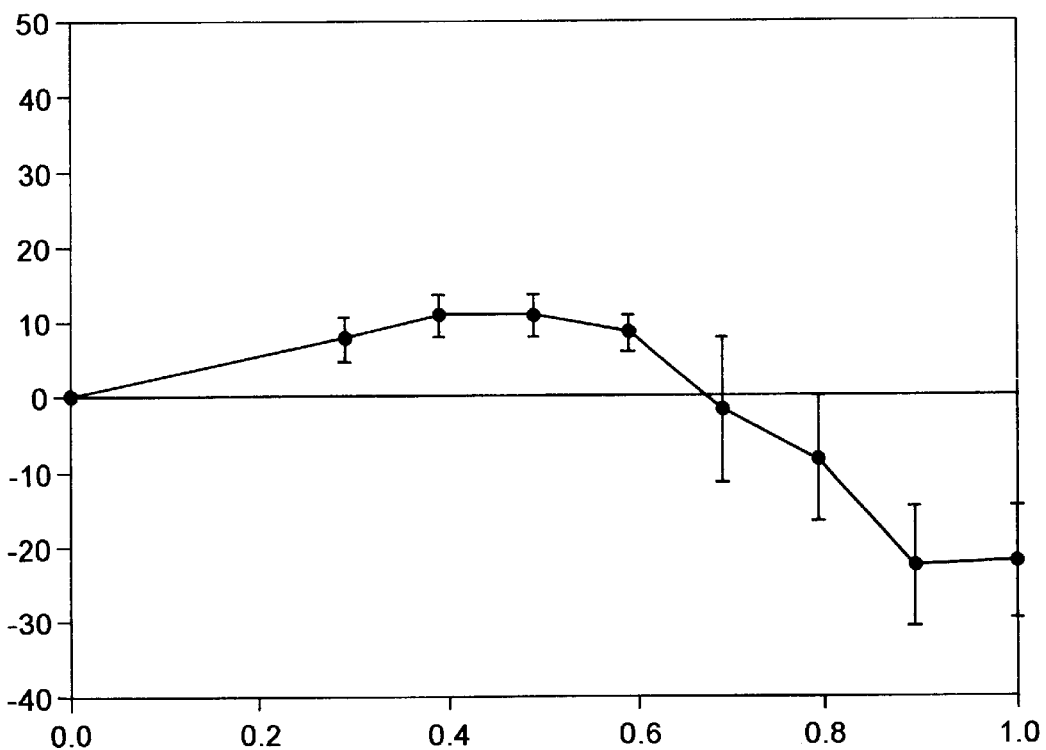
FIG. 4: curve of the recapture of glutamate by the astrocytes as a function of the concentration of IC023 (•), and in the presence of a fixed quantity of X/XO producing 50% blocking of glutamate recapture; the percentage of recapture of [$^3$H]glutamate is shown on the ordinate, and the concentration (in mM) of IC023 is shown on the abscissa.
Figure 5:
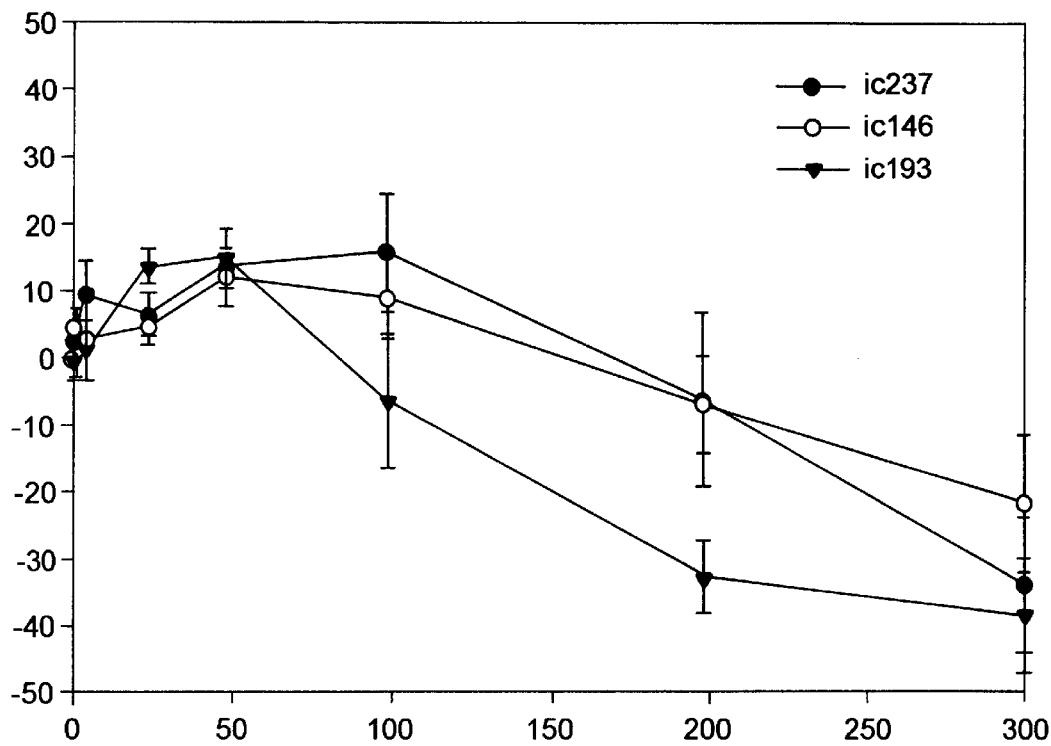
FIG. 5: curve of the recapture of glutamate by the astrocytes as a function of the concentration of compounds IC237 (•), IC146 (o), IC193 (▼), and in the presence of a fixed quantity of X/XO producing 50% blocking of glutamate recapture; the percentage of recapture of [$^3$H]glutamate is shown on the ordinate, and the concentration (in AM) of the compounds is shown on the abscissa.
Figure 6:
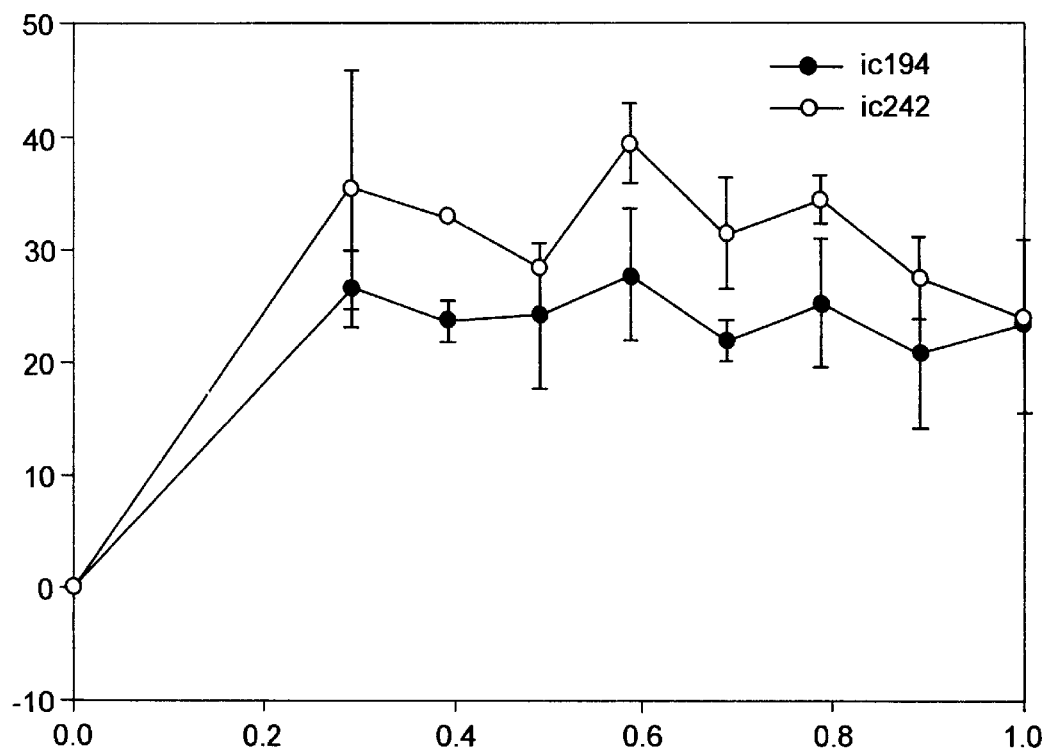
FIG. 6: curve of the recapture of glutamate by the astrocytes as a function of the concentration of compounds IC194 (•), IC242 (o), and in the presence of a fixed quantity of X/XO producing 50% blocking of glutamate recapture; the percentage of recapture of [$^3$H]glutamate is shown on the ordinate, and the concentration (in mM) of the compounds is shown on the abscissa.
Figure 7:
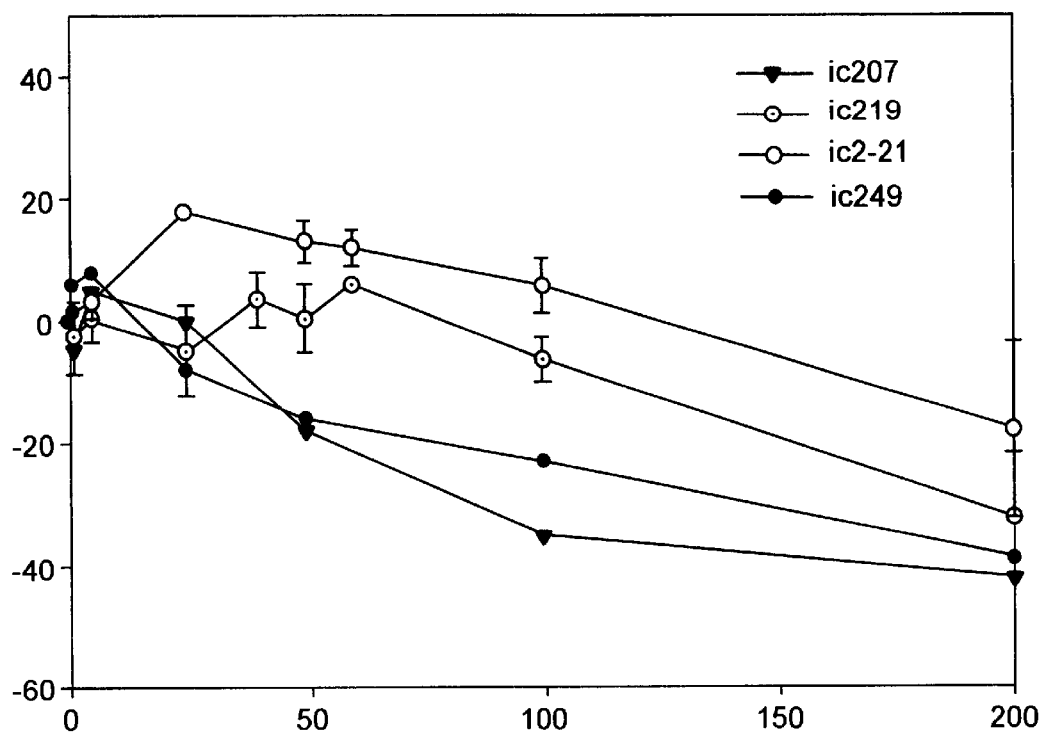
FIG. 7: curve of the recapture of glutamate by the astrocytes as a function of the concentration of compounds IC207 (▼), IC219 (⊙), IC2–21 (o), IC249 (•), and in the presence of a fixed quantity of X/XO producing 50% blocking of glutamate recapture; the percentage of recapture of [$^3$H]glutamate is shown on the ordinate, and the concentration (in μM) of the compounds is shown on the abscissa.
Figure 8:
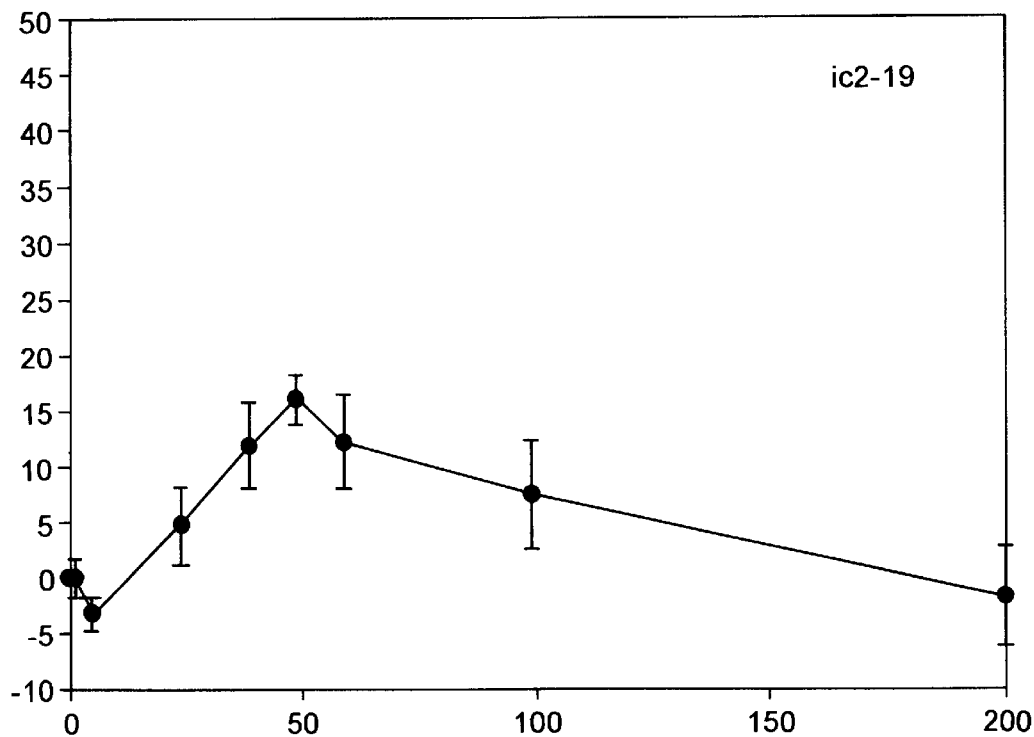
FIG. 8: curve of the recapture of glutamate by the astrocytes as a function of the concentration of compounds IC2–19 (•), and in the presence of a fixed quantity of X/XO producing 50% blocking of glutamate recapture; the percentage of recapture of [$^3$H]glutamate is shown on the ordinate, and the concentration (in μM) of IC2–19 is shown on the abscissa.
Figure 9:
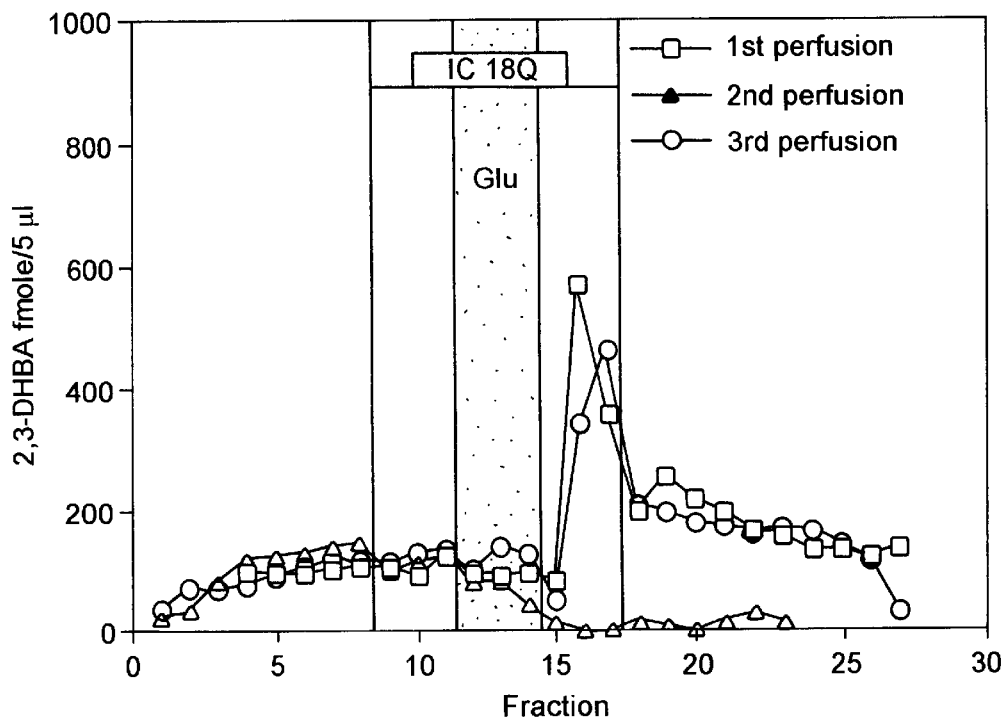
FIG. 9: curve of the secretion of free radicals in response to stimulation by glutamate. Blocking by injection of the drug IC180; first perfusion (□), second perfusion (▲), third perfusion (o); the fractions collected are shown on the abscissa; the concentration in fmol/5 μl of 2,3-DBHA formed is shown on the ordinate.
Figure 10:
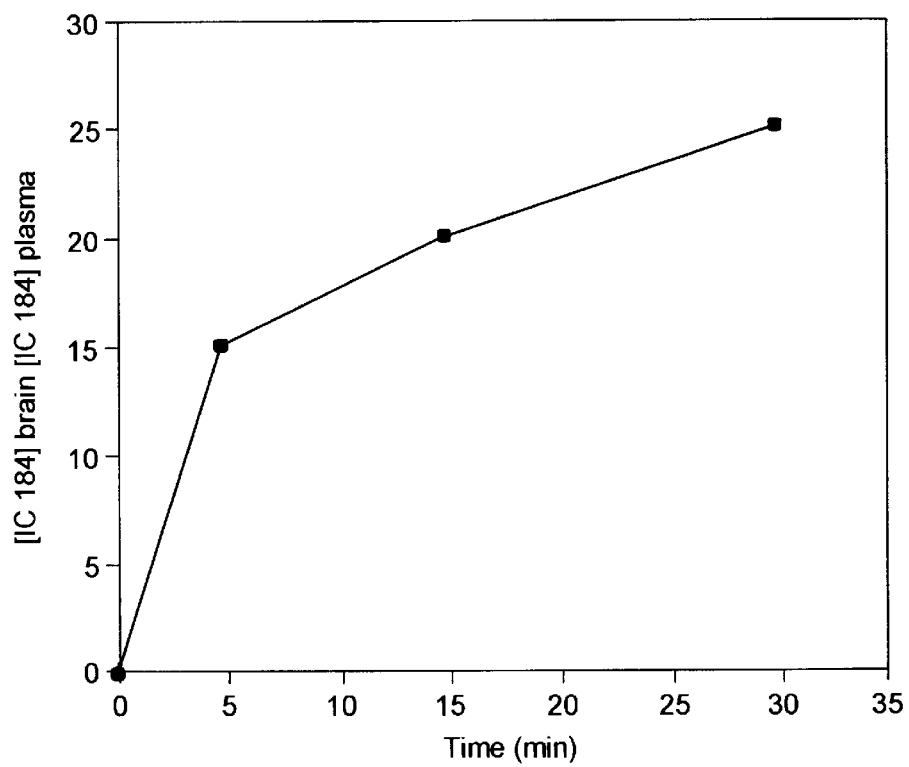
FIG. 10: curve of the ratio of the concentrations of IC180 in the brain and the plasma ([IC180]brain/[IC180]plasma, shown on the ordinate), as a function of time (shown in minutes on the abscissa).

What is claimed is:

1. A compound of the formula

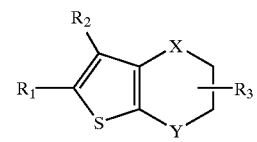

I wherein $R_1$ and $R_2$ are individually selected from the group consisting of hydrogen, alkyl of 1 to 5 carbon atoms, —OH and halogen or $R_1$ and $R_2$ together with the carbons to which they are attached form an aromatic or non-aromatic ring of 4 to 8 carbon atoms unsubstituted or substituted with a member of the group consisting of piperidino, N-methyl-piperidino and morpholino, $R_3$ is hydrogen or alkyl of 1 to 5 carbon atoms, one of X and Y is —CH2—, and the other is

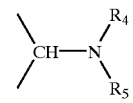

$R_4$ and $R_5$ are individually selected from the group consisting of hydrogen and alkyl of 1 to 5 carbon atoms or $R_4$ and $R_5$ together with the nitrogen to which they are attached form an aromatic or non-aromatic, unsubstituted or substituted heterocycle with 4 to 8 ring carbon atoms and optionally a second heteroatom selected from the group consisting of nitrogen, oxygen and sulfur, the substituents being selected from the group consisting of —CH$_3$ and —OH with the proviso that when one of X and Y is —CH2— and the other is

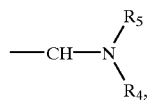

then $R_4$ and $R_5$ are not both hydrogen.

2. A compound of claim 1 having a formula selected from the group consisting of

IC023
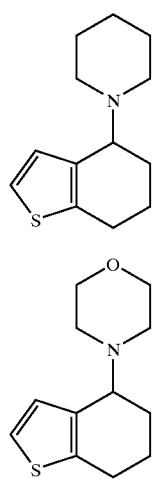

IC180
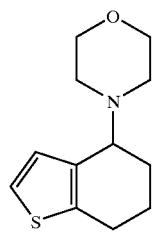

IC194
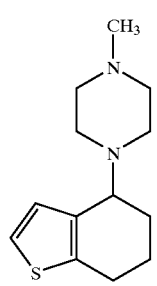

IC193
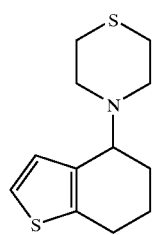

IC209
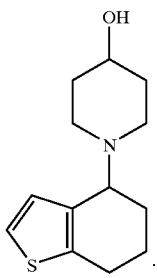

3. A compound of claim 1 having the formula:

III
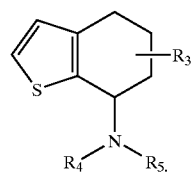

4. A compound of claim 3 having the formula:

IC146
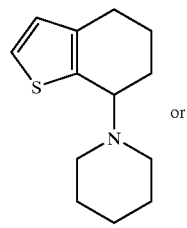

or

IC2-16
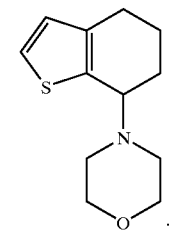

5. A compound of claim 1 having the formula:

(V)
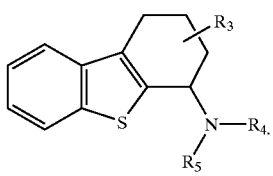

6. A compound of claim 5 having a formula selected from the group consisting of

IC207
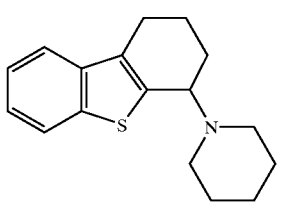

IC219
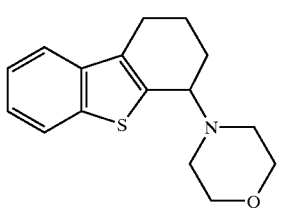

-continued

IC2-38

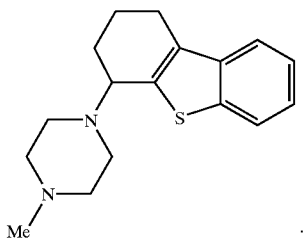

7. A compound of claim 1 wherein $R_1$ and $R_2$ together with the carbon atoms to which they are attached from benzene.

8. A compound of claim 1 wherein $R_4$ and $R_5$ with the nitrogen form

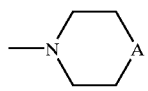

wherein A is a heteroatom selected from the group consisting of nitrogen, oxygen and sulfur

Z is —CH— or nitrogen and $R_6$ is selected from the group consisting of hydrogen, —OH and methyl.

9. A compound of claim 1 wherein $R_1$ and $R_2$ are hydrogen or form with the carbon atoms to which they are attached benzene, $R_3$ is hydrogen or alkyl of 1 to 5 carbon atoms, $R_4$ and $R_5$ are hydrogen or taken with the nitrogen to which they are attached form

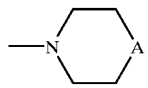

A is

and Z is

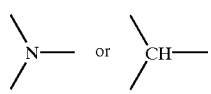

and $R_6$ is selected from the group consisting of hydrogen, —CH$_3$ and —OH.

10. A compound of claim 1 having the formula

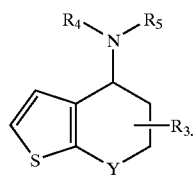

II wherein $R_3$, $R_4$ and $R_5$ are defined as in claim 1 and Y is —CH2—.

11. A composition for reducing greater than normal concentrations of extracellular glutamate comprising an effective amount of a compound of the formula

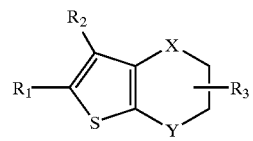

I wherein $R_1$ and $R_2$ are individually selected from the group consisting of hydrogen, alkyl of 1 to 5 carbon atoms, —OH and halogen or $R_1$ and $R_2$ together with the carbons to which they are attached form an aromatic or non-aromatic ring of 4 to 8 carbon atoms unsubstituted or substituted with a member of the group consisting of piperidino, N-methyl-piperdino and morpholino, $R_3$ is hydrogen or alkyl of 1 to 5 carbon atoms, one of X and Y is CH2 and the other is

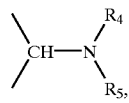

$R_4$ and $R_5$ are individually selected from the group consisting of hydrogen and alkyl of 1 to 5 carbon atoms or $R_4$ and $R_5$ together with the nitrogen to which they are attached form an aromatic or non-aromatic, unsubstituted or substituted heterocycle with 4 to 8 ring carbon atoms and optionally a second heteroatom selected from the group consisting of nitrogen, oxygen and sulfur, the substituents being selected from the group consisting of —CH$_3$ and —OH with the proviso that when one of X and Y is —CH2— and the other is

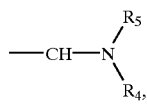

then $R_4$ and $R_5$ are not both hydrogen and an inert pharmaceutical carrier.

12. A method of reducing greater than normal concentrations of extra cellular glutamate in warm-blooded animals comprising administering to warm-blooded animals in need thereof an amount of a compound of the formula

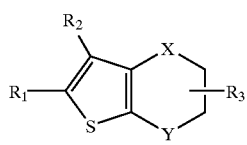

(I)

wherein $R_1$ and $R_2$ are individually selected from the group consisting of hydrogen, alkyl of 1 to 5 carbon atoms, —OH and halogen or $R_1$ and $R_2$ together with the carbons to which they are attached form an aromatic or non-aromatic ring of 4 to 8 carbon atoms unsubstituted or substituted with a member of the group consisting of piperidino, N-methyl-piperidino and morpholino, $R_3$ is hydrogen or alkyl of 1 to 5 carbon atoms, one of X and Y is —CH2—, and the other is

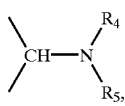

$R_4$ and $R_5$ are individually selected from the group consisting of hydrogen and alkyl of 1 to 5 carbon atoms or $R_4$ and $R_5$ together with the nitrogen to which they are attached form an aromatic or non-aromatic, unsubstituted or substituted heterocycle with 4 to 8 ring carbon atoms and optionally a second heteroatom selected from the group consisting of nitrogen, oxygen and sulfur, the substituents being selected from the group consisting of —CH$_3$ and —OH sufficient to reduce greater than normal concentrations of extra cellular glutamate.

13. The method of claim 12 wherein the compound is administered at a daily dose of 0.1 to 50 mg/day.

14. A method of claim 12 wherein the compound has a formula selected from the group consisting of

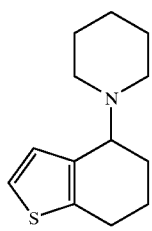

IC023

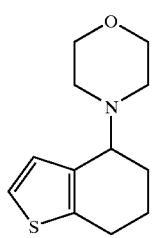

IC180

-continued

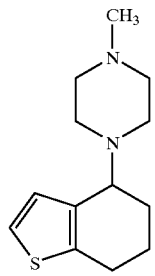

IC194

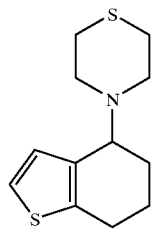

IC193

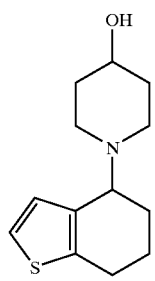

IC209

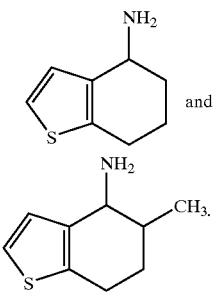

IC140 and

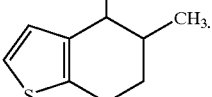

15. The method of claim 12 wherein the compound has the formula:

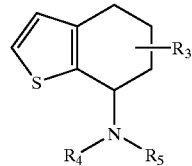

(III)

in which $R_3$ is hydrogen or alkyl of 1 to 5 carbon atoms, $R_4$ and $R_5$ are individually hydrogen or alkyl of 1 to 5 carbon atoms or $R_4$ and $R_5$ together with the nitrogen to which they are attached form an aromatic or non-aromatic, unsubstituted or substituted heterocycle with 4 to 8 ring carbon atoms and optionally a second heteroatom selected from the group consisting of nitrogen, oxygen and sulfur, the substituents being selected from the group consisting of —CH$_3$ and —OH.

16. The method of claim 12 wherein the compound has a formula selected from the group consisting of

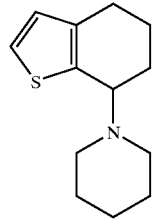
IC146

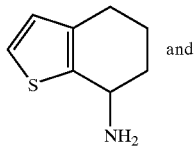
and
IC178

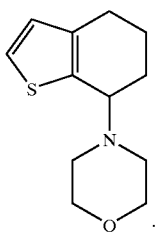
IC2-16

17. The method of claim 12 wherein the compound has the formula

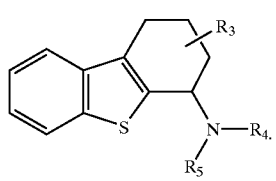
(V)

18. The method of claim 12 wherein the compound has a formula selected from the consisting of

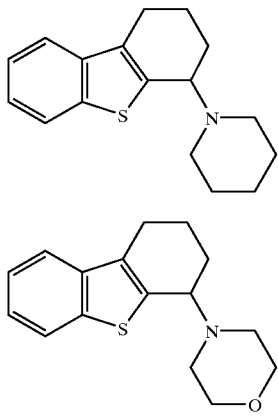
IC207

IC219

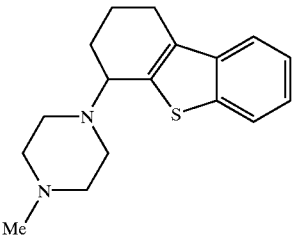
IC2-38

19. The method of claim 12 wherein $R_4$ and $R_5$ with the nitrogen form

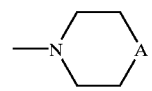

wherein A is a heteroatom selected from the group consisting of nitrogen, oxygen and sulfur or

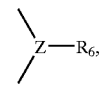

Z is —CH— or nitrogen and $R_6$ is selected from the group consisting of hydrogen, —OH and methyl.

20. The method of claim 12 having a compound of the formula

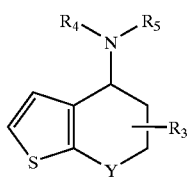
II wherein $R_3$ is hydrogen or alkyl of 1 to 5 carbon atoms, $R_4$ and $R_5$ are individually hydrogen or alkyl of 1 to 5 carbon atoms or $R_4$ and $R_5$ together with the nitrogen to which they are attached form an aromatic or non-aromatic, unsubstituted or substituted heterocycle with 4 to 8 ring carbon atoms and optionally a second heteroatom selected from the group consisting of nitrogen, oxygen and sulfur, the substituents being selected from the group consisting of —CH$_3$ and —OH.

* * * * *